US012485293B2

(12) United States Patent
Murayama

(10) Patent No.: US 12,485,293 B2
(45) Date of Patent: Dec. 2, 2025

(54) PHOTOTHERAPY DEVICE, PHOTOTHERAPY METHOD, AND COMPUTER-READABLE RECORDING MEDIUM

(71) Applicant: OLYMPUS CORPORATION, Tokyo (JP)

(72) Inventor: Kazuaki Murayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 301 days.

(21) Appl. No.: 18/220,425

(22) Filed: Jul. 11, 2023

(65) Prior Publication Data

US 2023/0347170 A1 Nov. 2, 2023

Related U.S. Application Data

(63) Continuation of application No. PCT/JP2021/016734, filed on Apr. 27, 2021.

(51) Int. Cl.
*A61N 5/06* (2006.01)

(52) U.S. Cl.
CPC ...... *A61N 5/062* (2013.01); *A61N 2005/0628* (2013.01); *A61N 2005/0662* (2013.01)

(58) Field of Classification Search
None
See application file for complete search history.

(56) References Cited

U.S. PATENT DOCUMENTS

2003/0153825 A1* 8/2003 Mooradian .......... A61B 5/0059 600/407
2008/0188745 A1 8/2008 Chen et al.
2011/0270092 A1 11/2011 Kang et al.
2019/0099612 A1* 4/2019 Hiereth .................... A61B 1/07
2022/0287549 A1* 9/2022 Ishikawa .................. A61N 5/06

FOREIGN PATENT DOCUMENTS

JP 2008-526326 A 7/2008
JP 2012-024283 A 2/2012
JP 2012-115406 A 6/2012
JP 2017-071654 A 4/2017
WO WO/2019/215905 * 11/2019 ............... A61B 5/00

OTHER PUBLICATIONS

International Search Report dated Jun. 22, 2021 received in PCT/JP2021/016734.
Japanese Office Action dated Jul. 2, 2024 received in 2023-516890.

* cited by examiner

*Primary Examiner* — Michael W Kahelin
(74) *Attorney, Agent, or Firm* — Scully, Scott, Murphy & Presser, P.C.

(57) ABSTRACT

A phototherapy device includes: a treatment light emitter configured to emit treatment light for causing a reaction of a drug; a narrow band light emitter configured to emit narrow band light having part of wavelength band of a visible light range; an excitation light emitter configured to emit excitation light for causing excitation of the drug; a first imager configured to obtain a narrow band light image which is formed using the narrow band light applied onto an application position of the treatment light; a second imager configured to obtain a fluorescence image which is formed using the excitation light emitted onto the application position of the treatment light; and a display image generator configured to generate a superimposed image in which the narrow band light image and the fluorescence image are superimposed.

9 Claims, 18 Drawing Sheets

PHOTOTHERAPY DEVICE, PHOTOTHERAPY METHOD, AND COMPUTER-READABLE RECORDING MEDIUM

CROSS-REFERENCE TO RELATED APPLICATION

This application is a continuation of International Application No. PCT/JP2021/016734, filed on Apr. 27, 2021, the entire contents of which are incorporated herein by reference.

BACKGROUND

1. Technical Field

The present disclosure relates to a phototherapy device, a phototherapy method, and a computer-readable recording medium.

2. Related Art

In the related art, research is being carried out about photoimmunotherapy (PIT) in which an antibody drug is specifically bound to the protein substance of cancer cells and is activated by the application of a near-infrared light representing the treatment light. As a result, the cancer cells get destroyed, and the cancer is treated (for example, refer to Japanese Patent Application Laid-open No. 2017-71654). The antibody drug, which has the near-infrared light applied thereto, absorbs the light energy; undergoes molecular oscillation; and produces heat. The cancer cells get destroyed due to that heat. At that time, the antibody drug produces fluorescence on account of becoming excited. The intensity of the fluorescence is used as an index of the effect of treatment.

The effect of treatment is believed to have the following three actions.

1. direct damage to cancer cells
2. indirect damage caused by blood flow change
3. indirect damage caused by immune activation It is a known fact that, when the cancer grows, there is an increase in the blood capillaries and the mucous surface turns into a tangled pattern. As a result of "2. indirect damage caused by blood flow change" mentioned above, in the vicinity of the treatment light application area, the blood capillaries on the superficial portion of the mucous membrane undergo changes along with changes in the mucous membrane microstructure. The changes in the blood capillaries on the superficial portion of the mucous membrane and in the mucous membrane microstructure serve as important indexes of confirming the effect of treatment.

SUMMARY

In some embodiments, a phototherapy device includes: a treatment light emitter configured to emit treatment light for causing a reaction of a drug; a narrow band light emitter configured to emit narrow band light having part of wavelength band of a visible light range; an excitation light emitter configured to emit excitation light for causing excitation of the drug; a first imager configured to obtain a narrow band light image which is formed using the narrow band light applied onto an application position of the treatment light; a second imager configured to obtain a fluorescence image which is formed using the excitation light emitted onto the application position of the treatment light; and a display image generator configured to generate a superimposed image in which the narrow band light image and the fluorescence image are superimposed.

In some embodiments, provided is a phototherapy method implemented for applying treatment light, which causes a reaction of a drug, onto a treatment area to confirm an effect of treatment. The phototherapy method includes: obtaining a narrow band light image formed using narrow band light that is emitted onto an application position of treatment light causing a reaction of a drug, the narrow band light having part of wavelength band of a visible light range; obtaining a fluorescence image formed using excitation light that is emitted onto the application position of the treatment light and that causes excitation of the drug; and generating a superimposed image in which the narrow band light image and the fluorescence image are superimposed.

In some embodiments, provided is a non-transitory computer-readable recording medium that stores a computer program to be executed by a phototherapy device applying treatment light, which causes a reaction of a drug, onto a treatment area to generate information to be used in confirming an effect of treatment. The program causes the phototherapy device to execute: obtaining a narrow band light image formed using narrow band light that is emitted onto an application position of treatment light causing a reaction of a drug, the narrow band light having part of wavelength band of a visible light range; obtaining a fluorescence image formed using excitation light that is emitted onto the application position of the treatment light and that causes excitation of the drug; and generating a superimposed image in which the narrow band light image and the fluorescence image are superimposed.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
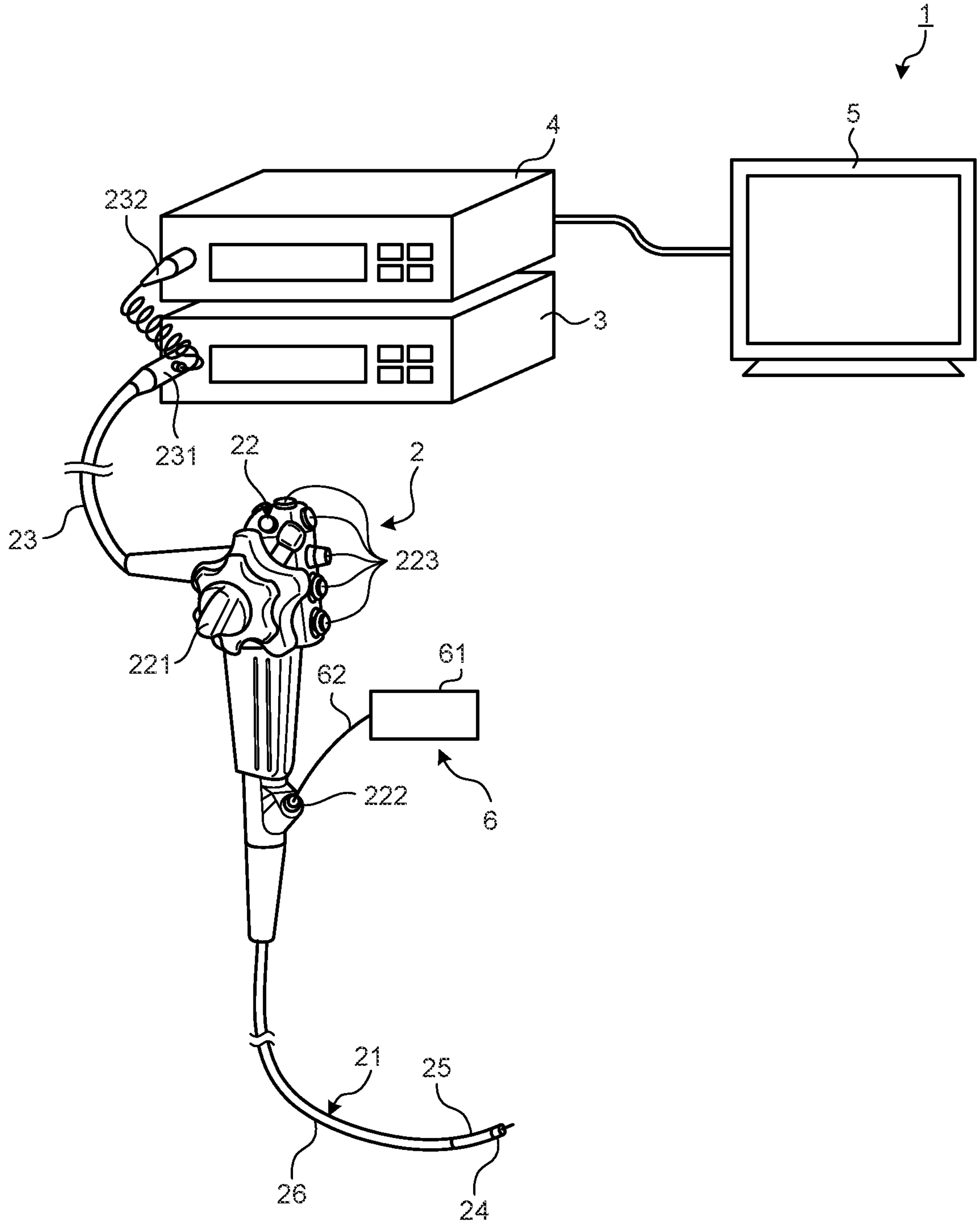
FIG. 1 is a diagram illustrating an overall configuration of an endoscope system according to a first embodiment of the disclosure.

Illustrative embodiments (hereinafter, embodiments) of the disclosure are described below with reference to the accompanying drawings. In the embodiments, as an example of a system that includes a phototherapy device according to the disclosure, the explanation is given about a medical endoscope system that takes images of the inside of a subject, such as a patient, and displays the images. Meanwhile, the disclosure is not limited by the embodiments described below. Moreover, in the drawings, identical constituent elements are referred to by the same reference numerals.

First Embodiment

Figure 2:
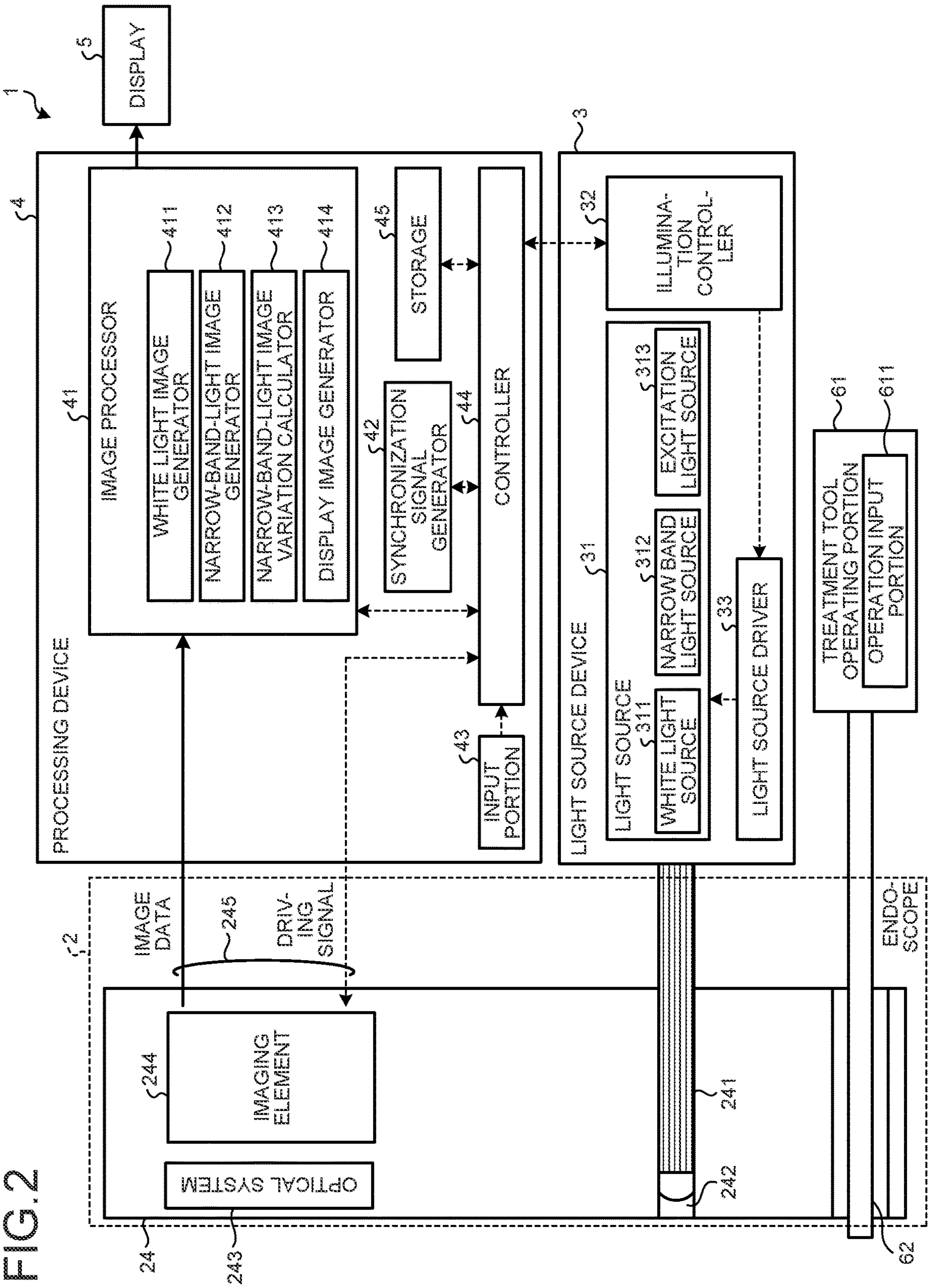
FIG. 2 is a block diagram illustrating an overall configuration of the endoscope system according to the first embodiment of the disclosure.
Figure 3:
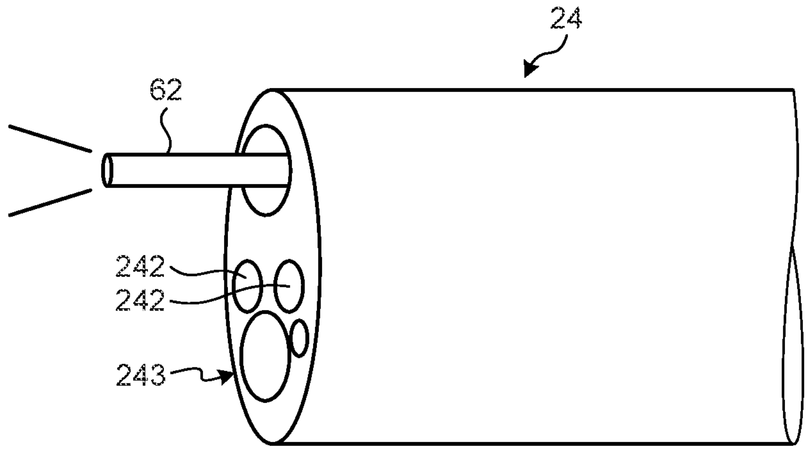
FIG. 3 is a diagram for explaining a front-end configuration of an endoscope according to the first embodiment of the disclosure.

FIG. 1 is a diagram illustrating an overall configuration of an endoscope system according to a first embodiment of the disclosure. FIG. 2 is a block diagram illustrating an overall configuration of the endoscope system according to the first embodiment. FIG. 3 is a diagram for explaining a front-end configuration of an endoscope according to the first embodiment.

An endoscope system 1 illustrated in FIGS. 1 and 2 includes: an endoscope 2 that, when the front end portion thereof is inserted inside the subject, takes in-vivo images of the subject; a light source device 3 that generates an illumination light to be emitted from the front end of the endoscope 2; a processing device 4 that performs predetermined signal processing with respect to imaging signals that are obtained by the endoscope 2 by performing imaging, and that comprehensively controls the overall operations of the endoscope system 1; a display 5 that displays in-vivo images generated as a result of the signal processing performed by the processing device 4; and a treatment tool device 6.

The endoscope 2 includes: a flexible and elongated insertion portion 21; an operating portion 22 that is connected to the proximal end of the insertion portion 21 and that receives input of various operation signals; and a universal cord 23 that extends from the operating portion 22 in the opposite direction to the direction of extension of the insertion portion 21, and that has various built-in cables connected to the light source device 3 and the processing device 4.

The insertion portion 21 includes the following: a front end portion 24 that has a built-in imaging element 244 in which pixels meant for receiving light and generating signals according to photoelectric conversion are arranged in a two-dimensional manner; a freely-bendable curved portion 25 that is made of a plurality of bent pieces; and a flexible tube 26 that is a flexible and long tube connected to the proximal end of the curved portion 25. The insertion portion 21 is inserted into the body cavity of the subject. Then, using the imaging element 244, the insertion portion 21 takes images of the body tissue present at such positions inside the photographic subject up to which the outside light does not reach.

The operating portion 22 includes the following: a bending knob 221 that makes the curved portion 25 bend in the vertical direction and the horizontal direction; a treatment tool insertion portion 222 through which a treatment tool such as a treatment-light application device, biopsy forceps, an electrical scalpel, or an inspection probe is inserted into the body cavity of the subject; and a plurality of switches 223 representing operation input portions that receive input of operation instruction signals regarding the peripheral devices including not only the processing device 4 but also an insufflation unit, a water supply unit, and a screen display control. The treatment tool inserted from the treatment tool insertion portion 222 passes through a treatment tool channel (not illustrated) in the front end portion 24 and comes out from an opening of the front end portion 24 (see FIG. 3).

The universal cord 23 at least has a built-in light guide 241 and a built-in cable assembly 245, which has one or more cables bundled therein. The universal cord 23 is branched at the end portion on the opposite side to the side of connection with the operating portion 22. At the branched end portion of the universal cord 23, a connector 231 is disposed that is detachably attachable to the light source device 3, and a connector 232 is disposed that is detachably attachable to the processing device 4. From the end portion of the connector 231, some part of the light guide 241 extends out. The universal cord 23 propagates the illumination light, which is emitted from the light source device 3, to the front end portion 24 via the connector 231 (the light guide 241), the operating portion 22, and the flexible tube 26. Moreover, the universal cord 23 transmits the image signals, which are obtained as a result of the imaging performed by the imaging element 244 that is disposed in the front end portion 24, to the processing device 4 via the connector 232. The cable assembly 245 includes a signal line for transmitting imaging signals; a signal line for transmitting driving signals meant for driving the imaging element 244; and a signal line for sending and receiving information such as the specific information related to the endoscope 2 (the imaging element 244). In the first embodiment, the explanation is given under the premise that a signal line is used for transmitting electrical signals. Alternatively, a signal line can be used for transmitting optical signals, or can be used for transmitting signals between the endoscope 2 and the processing device 4 in a wireless manner.

The front end portion 24 is made of fiberglass, and includes the following: the light guide 241 that constitutes a light guiding path for the light generated by the light source device 3; an illumination lens 242 that is disposed at the front end of the light guide 241; an optical system 243 that collects light; and the imaging element 244 that is disposed at the image formation position of the optical system 243 and that receives the light collected by the optical system 243, performs photoelectric conversion, and performs predetermined signal processing with respect to electrical signals.

The optical system 243 is configured using one or more lenses. The optical system 243 forms an observation image on the light receiving surface of the imaging element 244. Meanwhile, the optical system 243 can also be equipped with the optical zooming function meant for varying the angle of view and the focusing function meant for varying the focal point.

The imaging element 244 performs photoelectric conversion with respect to the light coming from the optical system 243, and generates electrical signals (image signals). In the imaging element 244, a plurality of pixels, each of which includes a photodiode for storing the electrical charge according to the amount of light and includes a capacitor for converting the electrical charge transferred from the photodiode into a voltage level, are arranged as a two-dimensional matrix. In the imaging element 244, each pixel performs photoelectric conversion with respect to the incoming light coming via the optical system 243 and generates an electrical signal. Then, the imaging element 244 sequentially reads the electrical signals generated by arbitrarily-set target pixels for reading from among a plurality of pixels, and outputs those electrical signals as image signals. The first imaging element 244*a* as well as the second imaging element 244*b* is configured using, for example, a CCD image sensor (CCD stands for Charge Coupled Device) or a CMOS image sensor (CMOS stands for Complementary Metal Oxide Semiconductor).

Meanwhile, the endoscope 2 includes a memory (not illustrated) that is used to store an execution program and a control program meant for enabling the imaging element 244 to perform various operations, and to store data containing the identification information of the endoscope 2. The identification information contains the specific information (ID), the model year, the specifications information, and the transmission method of the endoscope 2. Moreover, the memory can also be used to temporarily store the image data generated by the imaging element 244.

Given below is the explanation about a configuration of the light source device 3. The light source device 3 includes a light source 31, an illumination controller 32, and a light source driver 33. Under the control of the illumination controller 32, the light source 31 sequentially switches the illumination light and emits it onto the photographic subject (subject).

The light source 31 is configured using light sources and one or more lenses, and emits a light (illumination light) when one of the light sources is driven. The light generated by the light source 31 is emitted from the front end of the front end portion 24 toward the photographic subject via the light guide 241. The light source 31 includes a white light source 311, a narrow band light source 312, and an excitation light source 313. Herein, a light source, the light guide 241, and the illumination lens 242 constitute an emitter. For example, the narrow band light source 312, the light guide 241, and the illumination lens 242 constitute a narrow band light emitter.

The white light source 311 emits the light having the wavelength band of the visible light range (i.e., emits a white light). The white light source 311 is implemented using an LED light source, a laser light source, a xenon lamp, or a halogen lamp.

Figure 4:
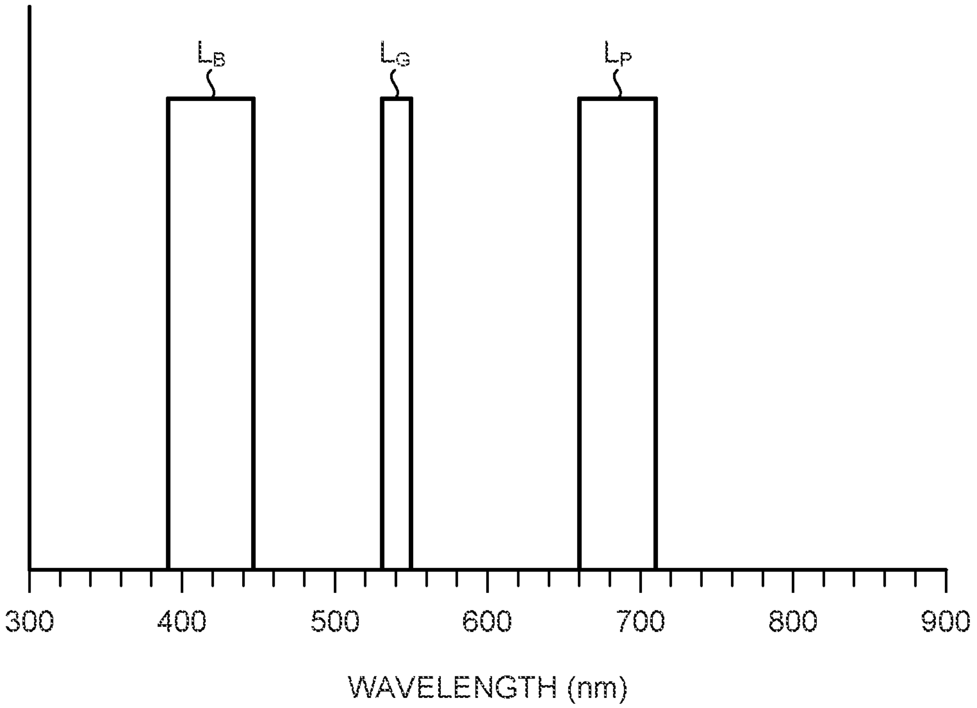
FIG. 4 is a diagram for explaining an example of the wavelength band of a light used as a narrow band light.

The narrow band light source 312 emits a light having some wavelengths or some part of the wavelength band from among the wavelength band of the visual light range. FIG. 4 is a diagram for explaining an example of the wavelength band of the light used as the narrow band light. The narrow band light is made of either one of the following lights or is made of a combination of the following lights: a light $L_B$ having the wavelength band equal to or greater than 390 nm and equal to or smaller than 445 nm; and a light $L_G$ having the wavelength band equal to or greater than 530 nm and equal to or smaller than 550 nm. Examples of the narrow band light include a light that is made of the lights $L_B$ and $L_G$ and that is used in NBI observation (NBI stands for Narrow Band Imaging). In the first embodiment, the explanation is given about the case in which a light made of the lights $L_B$ and $L_G$ is used as the narrow band light. Besides, the narrow band light can be made of either one of the following lights or can be made of a combination of some of the following lights: a light having the wavelength band equal to or greater than 490 nm and equal to or smaller than 590 nm; a light having the wavelength band equal to or greater than 590 nm and equal to or smaller than 620 nm; and a light having the wavelength band equal to or greater 620 nm and equal to or smaller than 780 nm. The narrow band light source 312 is implemented using an LED light source or a laser light source.

Meanwhile, in the case of causing excitation of the antibody drug during photoimmunotherapy, for example, a near-infrared light $L_P$ having the central wavelength of 690 nm is used (for example, the near-infrared light $L_P$ which is illustrated in FIG. 4 and which has the wavelength band equal to or greater than 660 nm and equal to or smaller than 710 nm is used).

Herein, if the light having the wavelength equal to or greater than 390 nm and equal to or smaller than 445 nm is emitted and if the scattering light or the returning light is obtained, then the blood vessels in the superficial portion of the mucous membrane can be visualized with a high degree of contrast. Alternatively, if the light having the wavelength band equal to or greater than 530 nm and equal to or smaller than 550 nm is emitted, or if the light having the wavelength band equal to or greater than 590 nm and equal to or smaller than 620 nm is emitted, or if the light having the wavelength band equal to or greater than 620 nm and equal to or smaller than 780 nm is emitted, and if the scattering light or the returning light is obtained; then the blood vessels in the relatively deeper portion of the mucous membrane can be visualized with a high degree of contrast.

The excitation light source 313 emits an excitation light meant for causing excitation of the excitation target (for example, an antibody drug during photoimmunotherapy). The excitation light source 313 is implemented using an LED light source or a laser light source. In the case of causing excitation of an antibody drug during photoimmunotherapy, for example, the near-infrared light $L_P$ is used.

Based on a control signal (modulated light signal) received from the processing device 4, the illumination controller 32 controls the electrical energy to be supplied to the light source 31, controls the light source to be made to emit light, and controls the driving timing of the light source.

Under the control of the illumination controller 32, the light source driver 33 supplies an electrical current to the light source to be made to emit light, and causes the light source 31 to output the light.

Given below is the explanation of a configuration of the processing device 4. The processing device 4 includes an image processor 41, a synchronization signal generator 42, an input portion 43, a controller 44, and a storage 45.

The image processor 41 receives, from the endoscope 2, image data of the illumination light of each color as obtained by the imaging element 244 by performing imaging. If analog image data is received from the endoscope 2, then the image processor 41 performs A/D conversion and generates digital imaging signals. Moreover, if image data in the form of optical signals is received from the endoscope 2, then the image processor 41 performs photoelectric conversion and generates digital image data.

The image processor 41 performs predetermined image processing with respect to the image data received from the endoscope 2, generates an image, and outputs the image to the display 5. Moreover, the image processor 41 sets boundary regions determined based on the image, and calculates the time variation in the fluorescence intensity. The image processor 41 includes a white light image generator 411, a narrow-band-light image generator 412, a fluorescence image generator 413, and a display image generator 414.

The white light image generator 411 generates a white light image based on an image formed using a white light.

The narrow-band-light image generator 412 generates a narrow band light image based on an image formed using a narrow band light.

Meanwhile, the optical system 243, the imaging element 244, and an image generator constitute an imager. For example, in the case of obtaining an image formed using the illumination of a narrow band light; the optical system 243, the imaging element 244, and the narrow-band-light image generator 412 constitute an imager for obtaining the narrow band light.

The fluorescence image generator 413 generates a fluorescence image formed using fluorescence.

The display image generator 414 generates an image to be displayed in the display 5. Herein, an image either implies an image based on the white light or the narrow band light, or implies an image formed by superimposing a narrow band light image and a fluorescence image.

The white light image generator 411, the narrow-band-light image generator 412, the fluorescence image generator 413, as well as the display image generator 414 performs predetermined image processing and generates an image. Herein, the predetermined image processing includes synchronization, gray level correction, or color correction. The synchronization represents the operation of achieving synchronization among the image data of the RGB color components. The gray level correction represents the operation of correcting the gray level of the image data. The color correction represents the operation of performing color compensation with respect to the image data. Meanwhile, the white light image generator 411, the narrow-band-light image generator 412, the fluorescence image generator 413, and the display image generator 414 can also perform gain adjustment according to the brightness of an image.

The image processor 41 is configured either using a general-purpose processor such as a central processing unit (CPU) or using a dedicated processor such as one of various arithmetic circuits, such as an application specific integrated circuit (ASIC), that implements specific functions. Moreover, the image processor 41 can be configured to include a frame memory for storing R image data, G image data, and B image data.

The synchronization signal generator 42 generates clock signals (synchronization signals) serving as the basis for the operations performed by the processing device 4, and outputs the generated synchronization signals to the light source device 3, the image processor 41, the controller 44, and the endoscope 2. Herein, the synchronization signals generated by the synchronization signal generator 42 include a horizontal synchronization signal and a vertical synchronization signal.

Thus, the light source device 3, the image processor 41, the controller 44, and the endoscope 2 perform operations in synchronization with each other based on the generated synchronization signals.

The input portion 43 is configured using a keyboard, a mouse, switches, or a touch-sensitive panel, and receives input of various signals such as an operation instruction signal that is meant for instructing the operations of the endoscope system 1. Meanwhile, the input portion 43 can also represent switches installed in the operating portion 22, or can be a portable terminal such as an external tablet computer.

The controller 44 performs driving control of the constituent elements including the imaging element 244 and the light source device 3, and performs input-output control of information with respect to the constituent elements. The controller 44 refers to control information data (for example, the reading timing) that is stored in the storage 45 and that is to be used in performing imaging control, and sends the control information data as driving signals to the imaging element 244 via predetermined signal lines included in the cable assembly 245. Moreover, the controller 44 switches among the following modes: a normal observation mode meant for observing the images obtained in white light illumination; a narrow band light observation mode meant for observing the images obtained in the illumination of the narrow band light; and a fluorescence observation mode meant for calculating the fluorescence intensity of the excitation target. The controller 44 is configured using a general-purpose processor such as a CPU or using a dedicated processor such as one of various arithmetic circuits, such as an ASIC, that implements specific functions.

The storage 45 is used to store various computer programs meant for causing the endoscope system 1 to perform operations, and to store data containing various parameters required in the operations performed by the endoscope system 1. Moreover, the storage 45 is used to store the identification information of the processing device 4, which contains the specific information (ID), the model year, and the specifications information of the processing device 4.

Moreover, the storage 45 is used to store various computer programs including an image obtaining program that is meant for enabling the processing device 4 to implement an image obtaining method. The computer programs can be recorded for circulation in a computer-readable recording medium such as a hard disk, a flash memory, a CD-ROM, a DVD-ROM, or a flexible disk. Alternatively, the computer programs can be downloaded via a communication network, which is implemented using, for example, an existing public line, or a local area network (LAN), or a wide area network (WAN); and which can be a wired network or a wireless network.

The storage 45 is implemented using a read only memory (ROM) in which various computer programs are installed in advance, and using a random access memory (RAM) or a hard disk in which various operation parameters and data are stored.

The display 5 displays a display image corresponding to the image signal received from the processing device 4 (the image processor 41) via a video cable. The display 5 is configured using a monitor such as a liquid crystal display or an organic electroluminescence (EL) display.

The treatment tool device 6 includes a treatment tool operating portion 61, and includes a flexible treatment tool 62 that extends from the treatment tool operating portion 61. The treatment tool 62 that is used in photoimmunotherapy represents a treatment light emitter which emits a light for enabling treatment (hereinafter, called the treatment light). The treatment tool operating portion 61 controls the emission of the treatment light from the treatment tool 62. The treatment tool operating portion 61 includes an operation input portion 611 that is configured using, for example, switches. In response to an input (for example, in response to the pressing of a switch) with respect to the operation input portion 611, the treatment tool operating portion 61 causes the treatment tool 62 to emit the treatment light. Meanwhile, in the treatment tool device 6, the light source that emits the treatment light either can be installed in the treatment tool 62 or can be installed in the treatment tool operating portion 61. The light source is implemented using a semiconductor laser or a light emitting diode (LED). For example, in the case of implementing photoimmunotherapy, the treatment light has the wavelength band equal to or greater than 680 nm and, for example, has the central wavelength of 690 nm (for example, the light $L_P$ illustrated in FIG. 4).

Herein, the illumination optical system included in the treatment tool 62 can be configured to enable varying the application range of the treatment light. For example, under the control of the treatment tool operating portion 61, the illumination optical system can be configured either using an optical system in which the focal distance can be varied or using a digital micromirror device (DMD); and it is possible to vary the spot diameter of the light applied onto the subject and to vary the shape of the application range.

Figure 5:
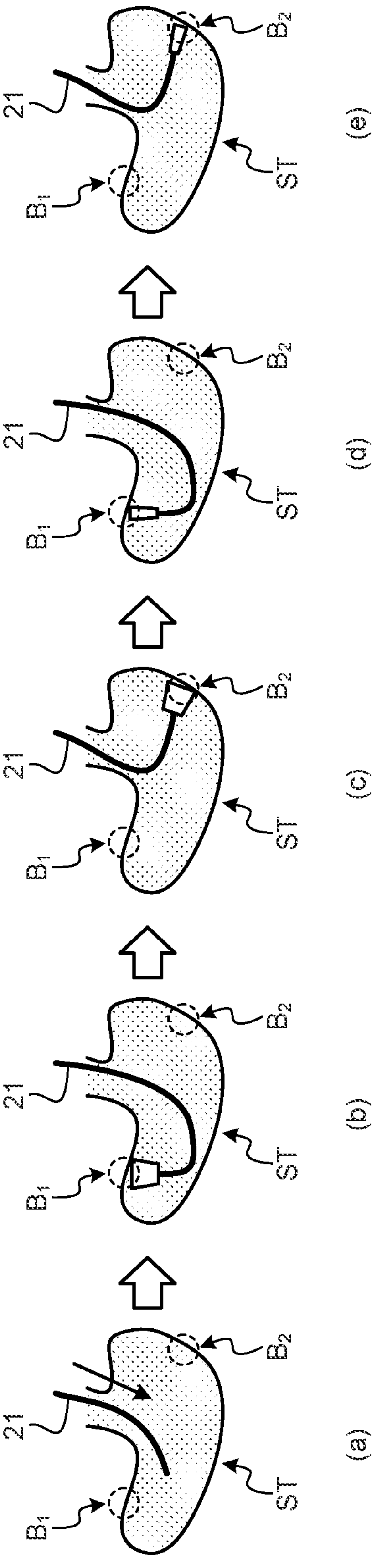
FIG. 5 is a diagram illustrating an exemplary flow of the treatment performed using the endoscope according to the first embodiment of the disclosure.

Explained below with reference to FIG. 5 is the flow of the treatment performed using the endoscope 2. FIG. 5 is a diagram illustrating an exemplary flow of the treatment performed using the endoscope according to the first embodiment of the disclosure. In FIG. 5 is illustrated an example of implementing photoimmunotherapy; and the insertion portion 21 is inserted into a stomach ST for carrying out the treatment.

Firstly, the operator inserts the insertion portion 21 into the stomach ST (see (a) in FIG. 5). At that time, the operator instructs the light source device 3 to emit the white light and, while observing the white light image that captures the inside of the stomach ST and that is displayed in the display 5, searches for the treatment position. Herein, it is assumed that the treatment is carried out for tumors $B_1$ and $B_2$ representing the treatment targets. At that time, an antibody drug is administered to the tumors $B_1$ and $B_2$ representing the treatment areas. The antibody drug can be administered using the endoscope 2 or using some other device, or the patient can be asked to take the antibody drug.

The operator observes the white light image and decides on the region that includes the tumors $B_1$ and $B_2$ as the application region. Moreover, as may be necessary, the operator applies the narrow band light or the excitation light onto the application region, and obtains a narrow band light image or a fluorescence image.

The operator orients the front end portion 24 toward the tumor $B_1$, projects the treatment tool 62 from the front end of the endoscope 2, and applies the treatment light onto the tumor $B_1$ (see (b) in FIG. 5). As a result of the application of the treatment light, the antibody drug that is bound to the tumor $B_1$ reacts, and the treatment of the tumor $B_1$ is carried out.

Then, the operator orients the front end portion 24 toward the tumor $B_2$, projects the treatment tool 62 from the front end of the endoscope 2, and applies the treatment light onto the tumor $B_2$ (see (c) in FIG. 5). As a result of the application of the treatment light, the antibody drug that is bound to the tumor $B_2$ reacts, and the treatment of the tumor $B_2$ is carried out.

Subsequently, the operator orients the front end portion 24 toward the tumor $B_1$ and applies the narrow band light or the excitation light onto the tumor $B_1$ from the front end of the endoscope 2 (see (d) in FIG. 5). Then, the operator obtains a post-treatment narrow band light image or a post-treatment fluorescence image and confirms the effect of treatment on the tumor $B_1$. As far as confirming the effect of treatment is concerned, for example, the operator makes the determination based on the variation between images (explained later).

Subsequently, the operator orients the front end portion 24 toward the tumor $B_2$ and applies the narrow band light or the excitation light onto the tumor $B_2$ from the front end of the endoscope 2 (see (e) in FIG. 5). Then, the operator obtains a post-treatment narrow band light image or a post-treatment fluorescence image and confirms the effect of treatment on the tumor $B_2$.

Herein, as may be necessary, the operator again applies the treatment light and confirms the effect of treatment in a repeated manner.

Figure 6:
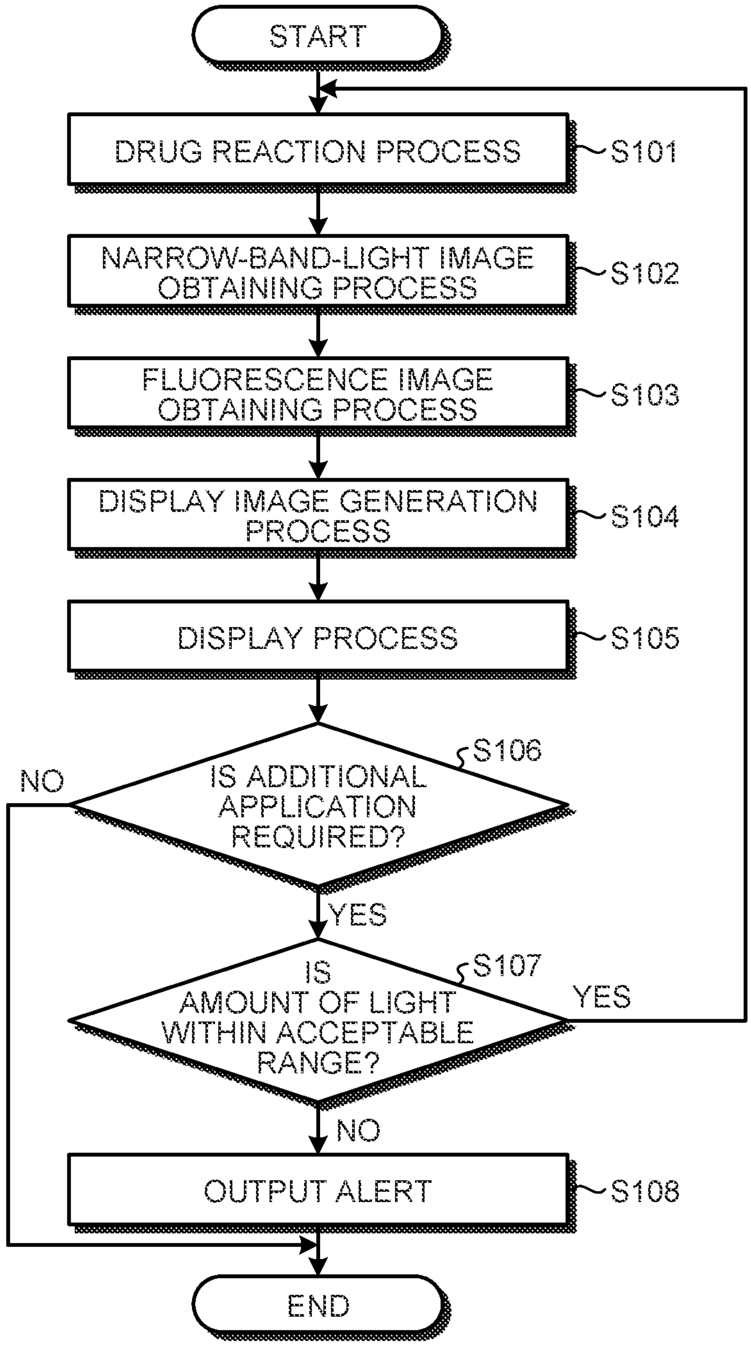
FIG. 6 is a flowchart for explaining an example of the operations performed by a processing device according to the first embodiment.

Explained below with reference to FIG. 6 are the operations performed by the processing device 4. FIG. 6 is a flowchart for explaining an example of the operations performed by the processing device according to the first embodiment.

Firstly, as a result of an operation performed by the operator, the treatment light is applied from the treatment tool 62 onto the antibody drug that is bound to the cancer cells, thereby causing a reaction of the drug (Step S101: drug reaction process). During the drug reaction process, a near-infrared light representing the treatment light is applied to activate the antibody drug, and the treatment for destroying the cancer cells is carried out.

Subsequently, a narrow band light is applied from the front end portion 24 onto the treatment position and a post-treatment narrow band light image (a second narrow band light image) is obtained (Step S102: narrow-band-light image obtaining process). The controller 44 causes the light source device 3 to emit the narrow band light, and causes the endoscope 2 to take an image of the narrow band light.

Subsequently, the light source device 3 is made to emit the excitation light, and the fluorescence of the antibody drug is detected (Step S103: fluorescence detection process). When emitted, the excitation light is applied onto the photographic subject from the endoscope 2, and the pre-treatment antibody drug gets excited and emits fluorescence. At that time, the processing device 4 obtains the imaging signal (fluorescence image) generated by the imaging element 244.

Herein, the narrow band light and the excitation light are alternately applied at Steps S102 and S103, thereby enabling holding down the leaking light and enhancing the image quality. Meanwhile, as far as enhancing the image quality is concerned, it is desirable that the narrow band light and the excitation light are separately applied. However, alternatively, the operations at Steps S102 and S103 can be performed in a simultaneous manner.

Figure 7:
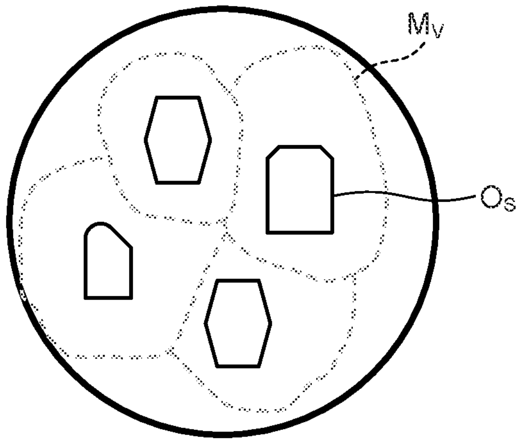
FIG. 7 is a diagram for explaining about the tissue in the normal state.

Given below is the explanation of the state of the tissue visualized as a result of performing NBI observation. FIG. 7 is a diagram for explaining about the tissue in the normal state. In the normal state in which cancer cells are not present, microstructures $O_S$ are uniformly structureless in entirety, and microvessels (in FIG. 7, illustrated as microvessels $M_V$ using dashed lines) remain invisible.

Figure 8A:
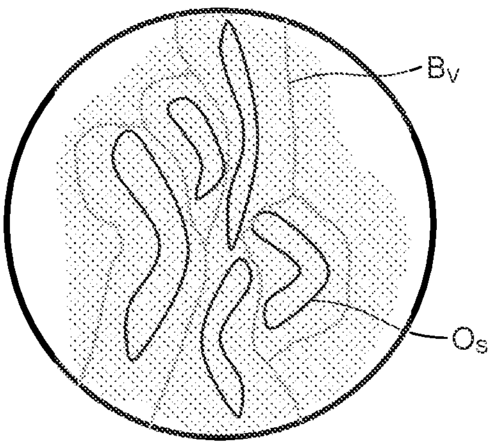
FIG. 8A is a diagram (1) for explaining about the tissue including cancer cells.
Figure 8B:
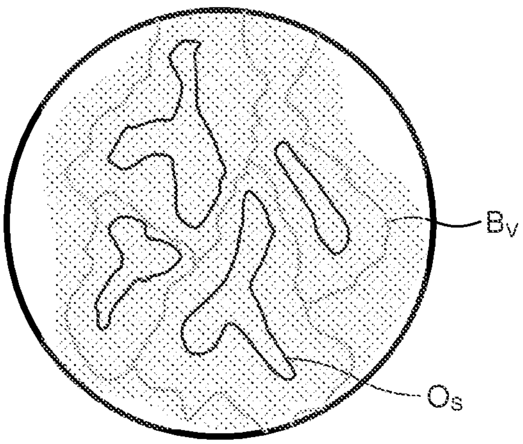
FIG. 8B is a diagram (2) for explaining about the tissue including cancer cells.
Figure 8C:
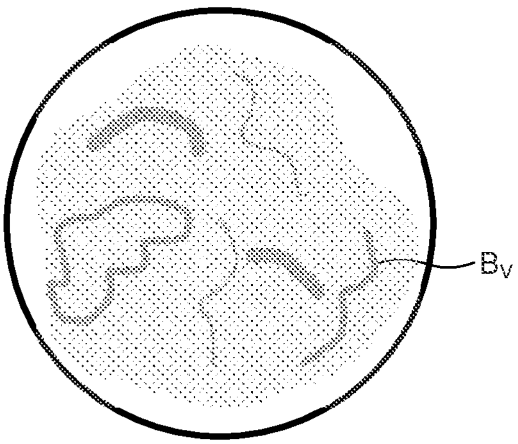
FIG. 8C is a diagram (3) for explaining about the tissue including cancer cells.

FIGS. 8A to 8C are diagrams for explaining about the tissue including cancer cells. In contrast to the normal state illustrated in FIG. 7, in the tissue in which cancer cells are present, the surface pattern of the microstructures $O_S$ and the state of the blood vessels is different as compared to the normal state. For example, as compared to an organized microstructure pattern, a blood vessel pattern may be formed in which blood vessels By enclose the microstructures (see FIG. 8A). Alternatively, as compared to an irregular microstructure pattern, a blood vessel pattern may be formed with a mesh design in which the blood vessels By enclose the microstructures (see FIG. 8B). Still alternatively, the microstructure pattern may become obscure, and the thickness of the blood vessels By may not be uniform (see FIG. 8C).

Moreover, in the state in which the antibody drug is bound to the protein substance of cancer cells, the application of the excitation light causes excitation of the antibody drug, and the antibody drug emits fluorescence (in FIG. 8A, illustrated in a hatched manner). When the treatment is not yet complete and when there is some residual antibody drug in the bound state, the fluorescence is detected. On the other hand, when the treatment is complete and there is no residual antibody drug, the fluorescence is not detected.

Figure 9:
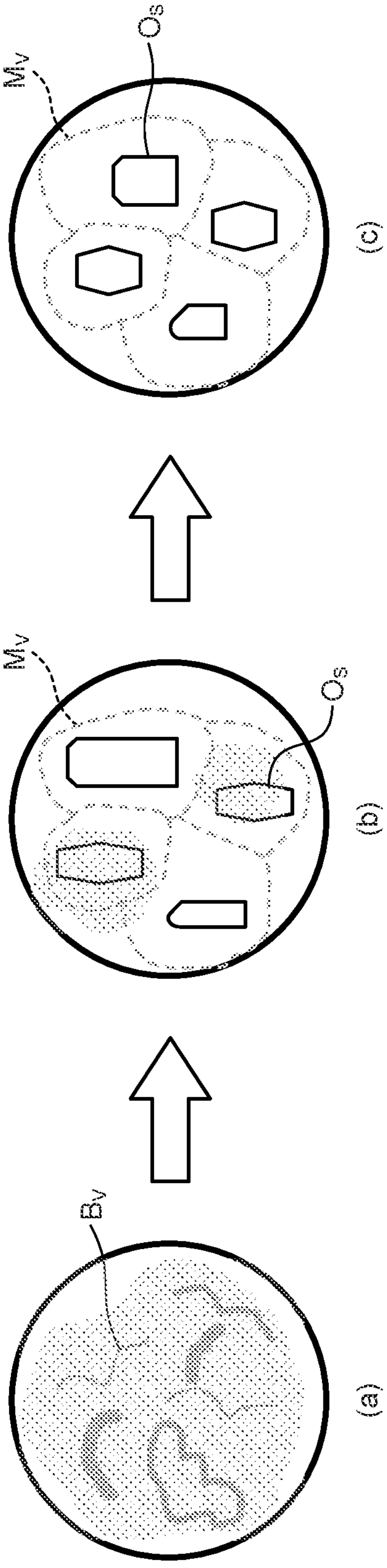
FIG. 9 is a diagram for explaining about the pre-treatment state and the post-treatment state of the tissue.

During photoimmunotherapy, for example, the treatment light is applied onto the tissue illustrated in FIG. 8C, and the normal state illustrated in FIG. 7 is restored. FIG. 9 is a diagram for explaining about the pre-treatment state and the post-treatment state of the tissue. In (a) in FIG. 9 is illustrated a narrow band light image obtained as a result of performing NBI observation before the treatment. In (b) and (c) in FIG. 9 are illustrated narrow band light images that are obtained in a stepwise manner as a result of performing NBI observation after the treatment. The operator confirms a transition from the state illustrated in (a) in FIG. 9 to the state illustrated in (c) in FIG. 9 in response to the application of the treatment light onto the tissue, and determines the effect of treatment and whether or not the treatment was successful. At that time, the state illustrated in (b) in FIG. 9 is such that, although uniform structurelessness is being achieved in entirety, fluorescence is still detected in some part. Hence, it is determined to additionally apply the treatment light.

Returning to the explanation with reference to FIG. 6, the display image generator 414 generates an image to be displayed in the display 5 (Step S104: display image generation process). The display image generator 414 generates a display image that includes a superimposed image (for example, the image illustrated in (b) or (c) in FIG. 9) which is formed by superimposing the narrow band light image obtained at Step S102 and the fluorescence light image obtained at Step S103.

The controller 44 displays the display image, which is generated at Step S104, in the display 5 (Step S105: display process). As a result of displaying the image in the display 5, the operator is asked to confirm the effect of treatment. The operator looks at the image and confirms the effect of treatment, and accordingly determines whether or not to again apply the treatment light and determines the region for applying the treatment light. Then, the operator operates the input portion 43 and inputs the determination result.

Figure 10:
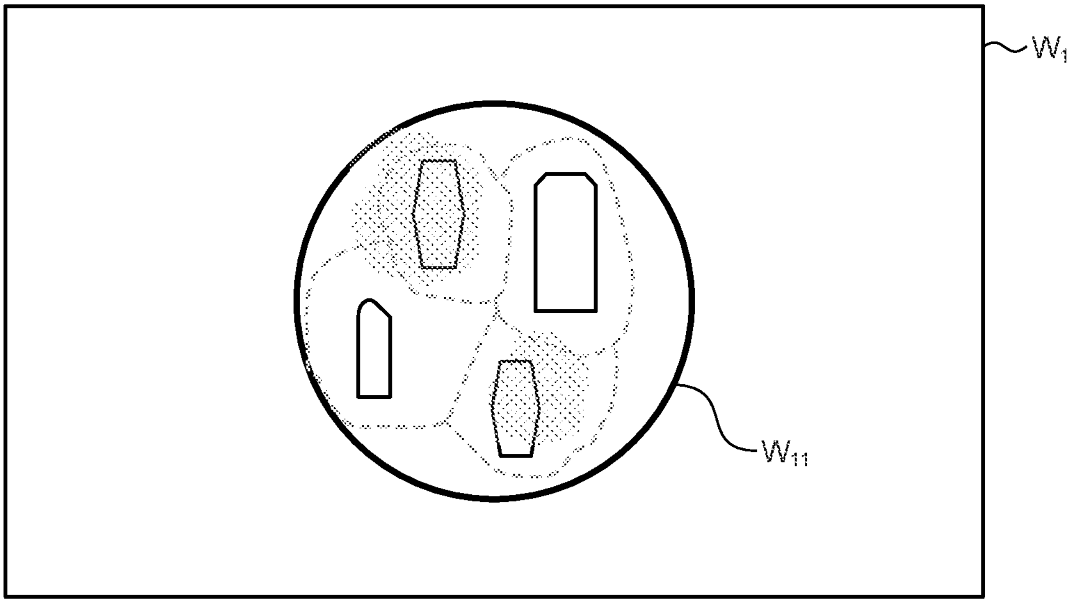
FIG. 10 is a diagram illustrating an exemplary display screen.

FIG. 10 is a diagram illustrating an exemplary display screen. For example, in the display 5, a display image $W_1$ is displayed that includes an image display portion $W_{11}$ for displaying the superimposed image formed by superimposing the post-treatment narrow band light image and the post-treatment fluorescence image. Thus, in the image display portion $W_{11}$, a superimposed image is displayed that is formed by superimposing the post-treatment narrow band light image obtained at Step S102 and the post-treatment fluorescence image obtained at Step S103. In the image illustrated in FIG. 10, since fluorescence (the hatched portion in FIG. 10) is observed, it is believed that there is residual antibody drug, and the operator considers about additional application of the treatment light based on the image.

When the input portion 43 receives input of the determination result, the controller 44 determines whether or not an additional application of the treatment light is to be performed (Step S106). Based on the input determination result, if it is determined that the additional application of the treatment light is not required (No at Step S106), then the operations are ended. On the other hand, if it is determined that the additional application of the treatment light is required (Yes at Step S106), then the system control proceeds to Step S107.

In the case of performing the additional application of the treatment light, for example, in the illumination optical system, control is performed to match the shape of the light application range to the shape of the boundary region, and the operator adjusts the spot diameter and applies the treatment light.

The controller 44 determines whether or not, in the region on which the additional application of the treatment light is to be performed, the amount of already-applied light is within the acceptable range (Step S107). The acceptable range represents a preset amount of light and is set to have at least the upper limit value. The upper limit value is set so as to hold down any damage to the tissue due to excessive application of the treatment light. Thus, for example, the controller 44 determines whether or not the amount of light already applied onto the operator-specified target region (i.e., the cumulative amount of light) is exceeding the upper limit value. The amount of already applied light is calculated based on, for example, the output and the application period of the treatment light as input by the operator.

If the controller 44 determines that the amount of light is within the acceptable range (i.e., smaller than the upper limit value) (Yes at Step S107), then the system control returns to Step S101 and the operations are repeated. On the other hand, if the controller 44 determines that the amount of already-applied light is exceeding the acceptable range (the upper limit value) (No at Step S107), then the system control proceeds to Step S108.

At Step S108, the controller 44 issues an alert indicating that the amount of applied light has exceeded the acceptable range. The alert can be displayed as character information in the display 5, or can be issued in the form of a sound or a light, or can be a combination thereof. After the alert is displayed in the display 5, the controller 44 ends the operations.

In the first embodiment described above, in the display 5, a superimposed image is displayed that is formed by superimposing a narrow band light image, in which the tissue structure is visualized, and a fluorescence image, in which the presence or absence of the antibody drug is visualized. Then, the operator is asked to determine whether or not the additional application of the treatment light is to be performed. According to the first embodiment, the effect of treatment can be appropriately confirmed not only based on the variation occurring in the tissue or the blood vessels after the treatment but also based on the residual state of the antibody drug.

Moreover, in the first embodiment, at the time of additional application of the treatment light, the cumulative amount of treatment light applied onto the concerned region is compared with the acceptable range. If the cumulative amount of treatment light has exceeded the acceptable range, then an alert is issued to indicate that the cumulative amount of treatment light has exceeded the acceptable range. Thus, according to the first embodiment, it becomes possible to hold down the damage to the tissue due to excessive application of the treatment light.

Meanwhile, in the first embodiment, the imaging element 244 can be configured using a multi-band image sensor, so that the lights having a plurality of mutually different wavelength bands can be individually obtained. For example, the scattering light or the returning light of the light having the wavelength band equal to or greater than 380 nm and equal to or smaller than 440 nm, and the scattering light or the returning light of the light having the wavelength band equal to or greater than 530 nm and equal to or smaller than 550 nm can be individually obtained using a multi-band image sensor; and a narrow band light image corresponding to each light can be generated. As a result, it becomes possible to obtain blood vessel images having different depths from the superficial portion of the mucous membrane, and to calculate the image variation with a higher degree of accuracy using the images of the blood vessels and the tissue at each depth. Moreover, even when the narrow band light and the excitation light are applied in a simultaneous manner, a narrow band light image and a fluorescence image can be obtained on an individual basis.

Second Embodiment

Figure 11:
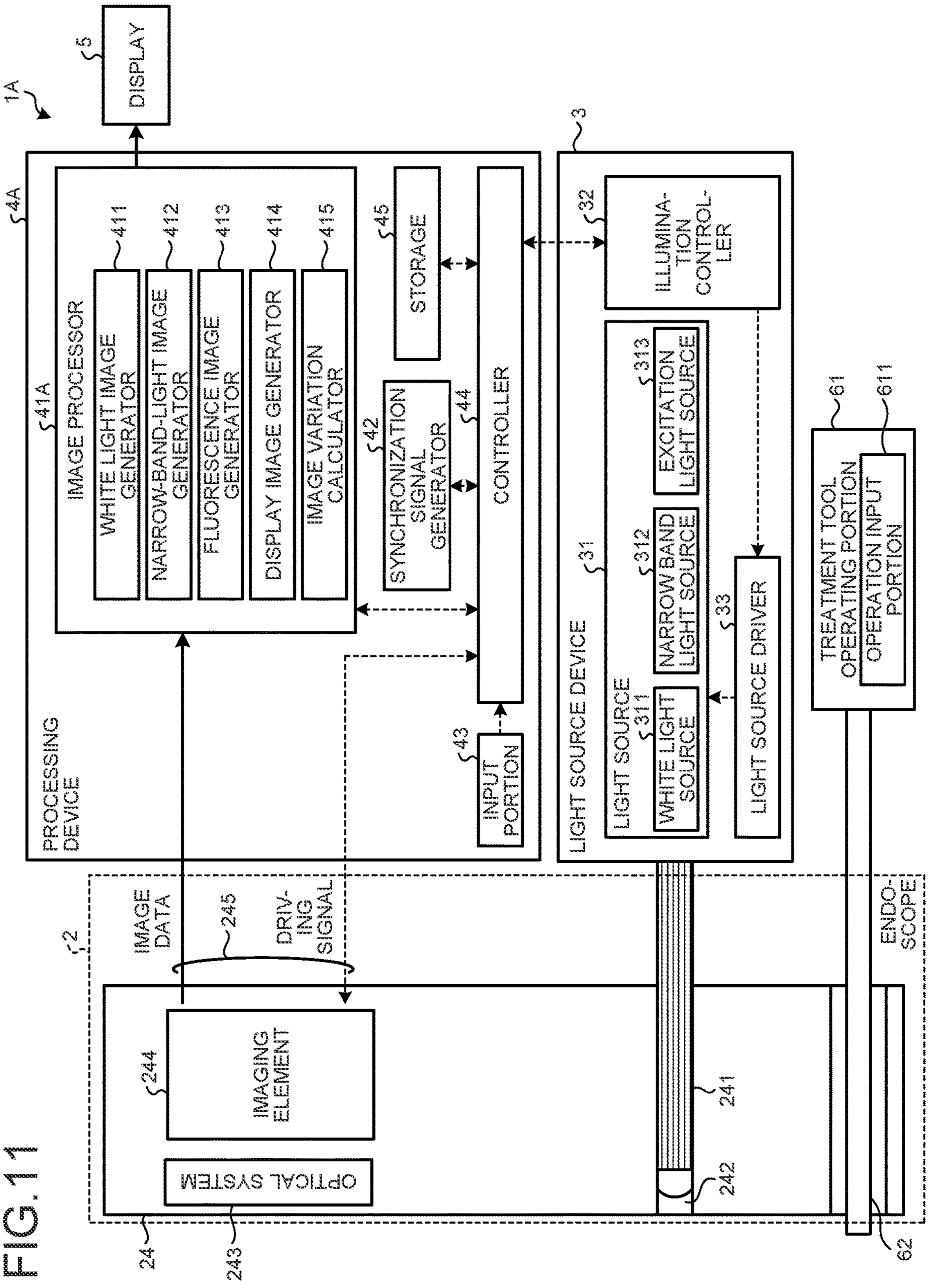
FIG. 11 is a block diagram illustrating an overall configuration of an endoscope system according to a second embodiment of the disclosure.

A second embodiment is described below with reference to FIGS. 11 to 14. FIG. 11 is a block diagram illustrating an overall configuration of an endoscope system according to the second embodiment of the disclosure. An endoscope system 1A according to the second embodiment includes a processing device 4A in place of the processing device 4 of the endoscope system 1 according to the first embodiment. Other than the processing device 4A, the configuration is same as the endoscope system 1. Hence, the same explanation is not given again.

Given below is the explanation of a configuration of the processing device 4A. The processing device 4A includes an image processor 41A, the synchronization signal generator 42, the input portion 43, the controller 44, and the storage 45.

The image processor 41A includes the white light image generator 411, the narrow-band-light image generator 412, the fluorescence image generator 413, the display image generator 414, and an image variation calculator 415.

The image variation calculator 415 calculates the time variation occurring in images. More particularly, the image variation calculator 415 calculates the time variation between narrow band light images that are generated by the narrow-band-light image generator 412 and that are taken at different timings, and/or calculates the time variation between fluorescence images that are generated by the fluorescence image generator 413 and that are taken at different timings.

Figure 12:
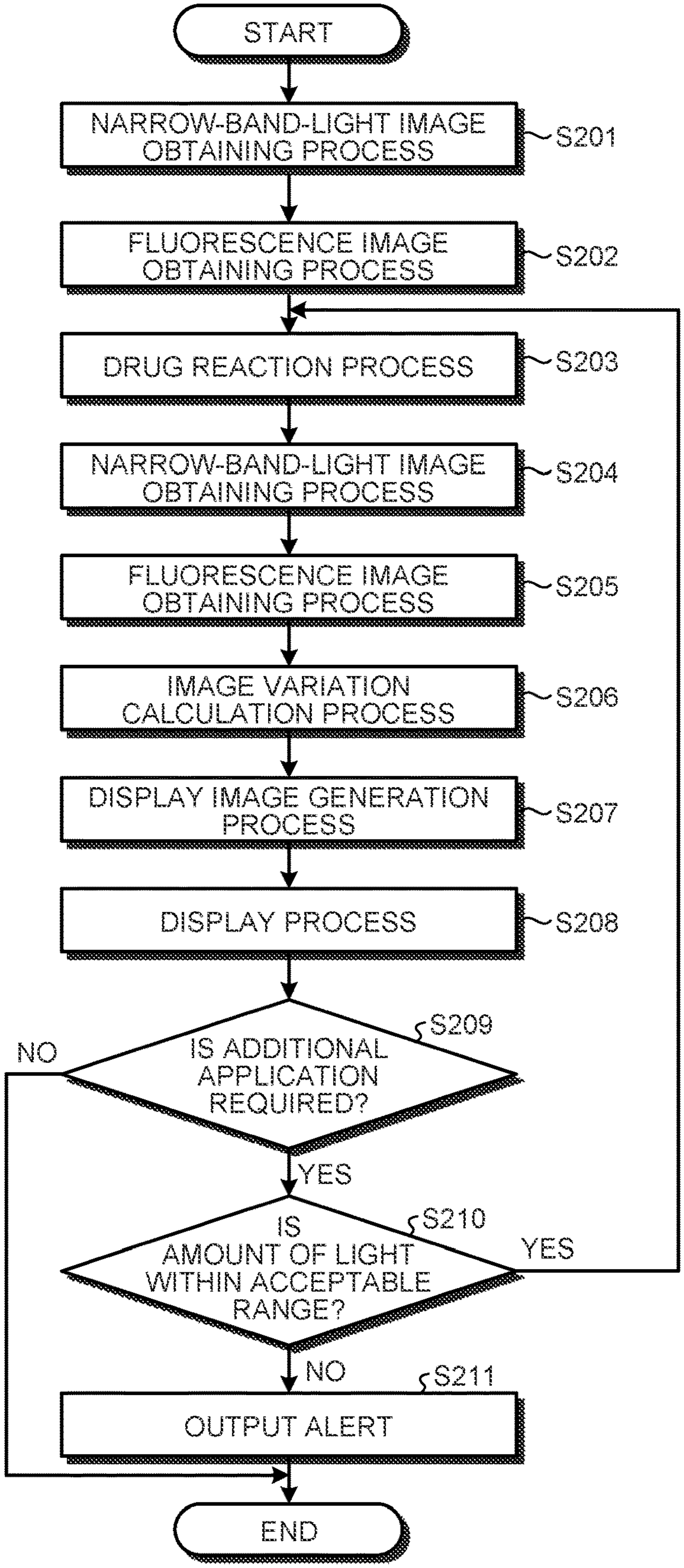
FIG. 12 is a flowchart for explaining an example of the operations performed by the processing device according to the second embodiment.

Explained below with reference to FIG. 12 are the operations performed by the processing device 12. FIG. 12 is a flowchart for explaining an example of the operations performed by the processing device according to the second embodiment.

Firstly, the narrow band light is applied from the front end portion 24 onto the treatment position and a pre-treatment narrow band light image (a first narrow band light image) is obtained (Step S201: narrow-band-light image obtaining process). Herein, the controller 44 causes the light source device 3 to emit the narrow band light, and causes the endoscope 2 to take an image of the narrow band light. After the imaging is performed, the narrow-band-light image generator 412 generates a narrow band light image.

Moreover, the excitation light is applied from the front end portion 24 onto the treatment position and a pre-treatment fluorescence image (a first fluorescence image) is obtained (Step S202: fluorescence image obtaining process). Herein, the controller 44 causes the light source device 3 to emit the excitation light, and causes the endoscope 2 to take an image of the fluorescence emitted by the antibody drug. After the imaging is performed, the fluorescence image generator 413 generates a fluorescence image.

Meanwhile, the operations at Steps S201 and S202 can alternatively be performed in the reverse order.

Then, as a result of an operation performed by the operator, the treatment light is applied from the treatment tool 62 onto the antibody drug that is bound to the cancer cells, thereby causing a reaction of the drug (Step S203: drug reaction process).

Subsequently, a narrow band light is applied from the front end portion 24 onto the treatment position and a post-treatment narrow band light image (a second narrow band light image) is obtained (Step S204: narrow-band-light image obtaining process). At Step S204 too, in an identical manner to Step S201, the controller 44 causes the light source device 3 to emit the narrow band light, and causes the endoscope 2 to take an image of the narrow band light.

Furthermore, the excitation light is applied from the front end portion 24 onto the treatment position and a post-treatment fluorescence image (a second fluorescence image) is obtained (Step S205: fluorescence image obtaining process). At Step S205 too, in an identical manner to Step S202, the controller 44 causes the light source device 3 to emit the excitation light, and causes the endoscope 2 to take an image of the fluorescence emitted by the antibody drug.

Meanwhile, the operations at Steps S204 and S205 can alternatively be performed in the reverse order.

Then, the image variation calculator 415 calculates the time variation between a pre-treatment image and a post-treatment image (Step S206: image variation calculation process). The image variation calculator 415 compares the pre-treatment narrow band light image and the post-treatment narrow band light image and calculates, as the image variation, values indicating the intelligibility and the homogeneity of the superficial tissue pattern, and values indicating the homogeneity and visibility of the thickness of the blood vessels. Moreover, the image variation calculator 415 can calculate, as the image variation, the difference between the pre-treatment fluorescence intensity and the post-treatment fluorescence intensity.

At that time, the image variation calculator 415 individually calculates, from the obtained narrow band light images, the variation occurring either in the state of the vascular structures or in the state of the microstructures $O_S$. The target for calculating the variation can be set by selection from the options, namely, only the vascular structures, only the microstructures, and the vascular structures as well as the microstructures. The image variation calculator 415 extracts the feature points of images; compares the variation occurring in the positions of the feature points and compares the sizes and the distribution of the feature points; and calculates the variation.

Figure 13A:
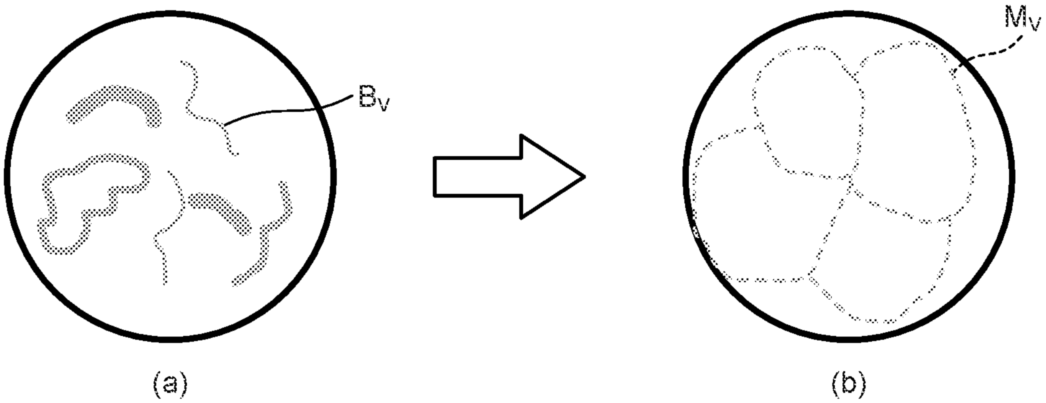
FIG. 13A is a diagram (1) illustrating the extraction of structures from a narrow band light image regarding the pre-treatment state of the tissue and the post-treatment state of the tissue.
Figure 13B:
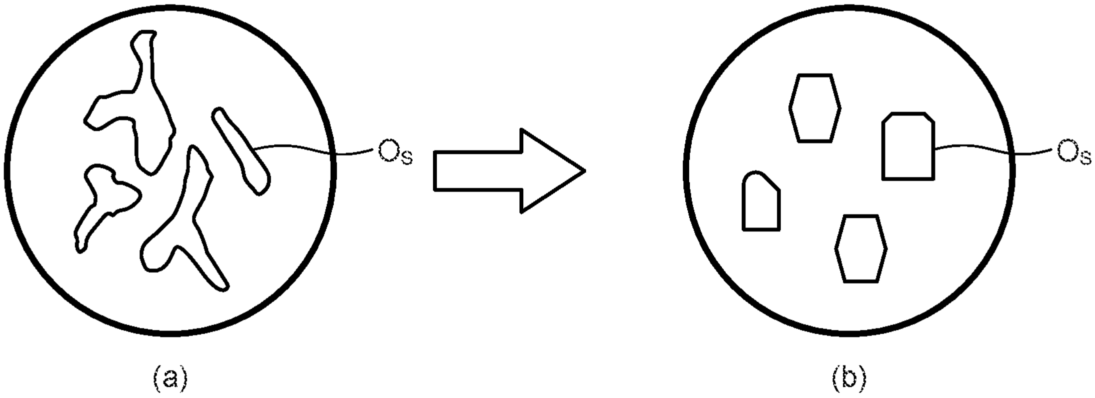
FIG. 13B is a diagram (2) illustrating the extraction of structures from a narrow band light image regarding the pre-treatment state of the tissue and the post-treatment state of the tissue.

FIGS. 13A and 13B are diagrams illustrating the extraction of structures from a narrow band light image regarding the pre-treatment state of the tissue and the post-treatment state of the tissue. In FIG. 13A are illustrated the images when the vascular structures are extracted. In FIG. 13B are illustrated the images when the microstructures are extracted. The image variation calculator 415 extracts the blood vessels $B_V$ from the pre-treatment narrow band light image as well as from the post-treatment narrow band light image; calculates the contrast value of the blood vessels; and then calculates the contrast ratio between the blood vessels By and the surrounding. Subsequently, the image variation calculator 415 calculates, as the image variation, the difference in the contrast ratios between the pre-treatment narrow band light image and the post-treatment narrow band light image (see FIG. 13A).

Moreover, the image variation calculator 415 extracts the microstructures $O_S$ of the superficial portion of the mucous membrane from the pre-treatment narrow band light image as well as from the post-treatment narrow band light image; and calculates the intelligibility of the microstructures $O_S$. Then, the image variation calculator 415 calculates, as the image variation, the difference in the intelligibility between the pre-treatment narrow band light image and the post-treatment narrow band light image (see FIG. 13B). At that time, in the narrow band light image, the post-treatment microstructures are visualized more clearly as compared to the pre-treatment microstructures. Meanwhile, for example, the image variation calculator 415 can extract the microstructures $O_S$ and calculate, as the variation, the degree of coincidence of the microstructures $O_S$ among the images.

If the image variation between narrow band light images is calculated and if the image variation between fluorescence images (i.e., the variation in the fluorescence intensity) is also calculated, then the image variation calculator 415 either can use both types of image variations and can calculate a single value representing the image variation, or can calculate independent values indicating different types of image variations.

Then, the display image generator 414 generates an image to be displayed in the display 5 (Step S207: display image generation process). The display image generator 414 generates an image in which a superimposed image of the narrow band light image and the fluorescence image is visually expressed and the calculated image variation is also visually expressed.

The controller 44 displays the image, which is generated at Step S207, in the display 5 (Step S208: display process). As a result of displaying the image in the display 5, the operator is asked to confirm the effect of treatment. The operator looks at the image and confirms the effect of treatment, and accordingly determines whether or not the additional application of the treatment light is to be performed and determines the region for applying the treatment light. Then, the operator operates the input portion 43 and inputs the determination result.

Figure 14:
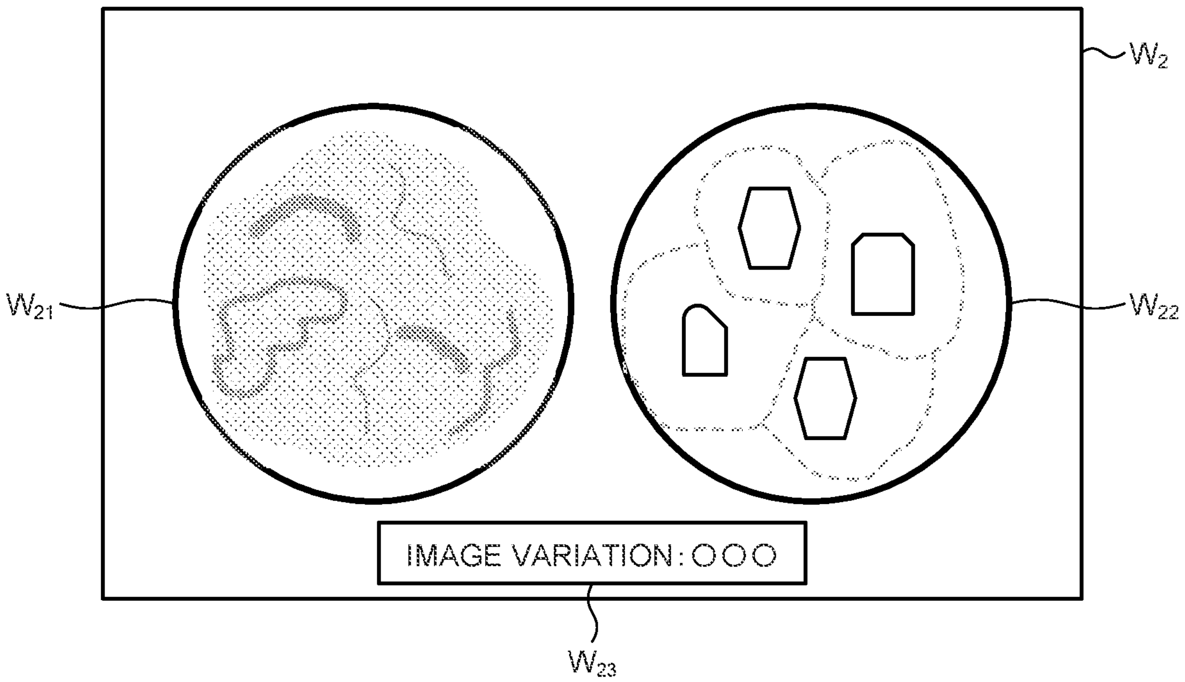
FIG. 14 is a diagram illustrating an exemplary display screen.

FIG. 14 is a diagram illustrating an exemplary display screen in which images indicating the pre-treatment state and the post-treatment state of the tissue are displayed. For example, in the display 5, a display image $W_2$ is displayed that includes: a first image display portion $W_{21}$ for displaying the pre-treatment image; a second image display portion $W_{22}$ for displaying the post-treatment image; and an information display portion $W_{23}$ for displaying the variation (for example, the contrast value mentioned earlier) between the pre-treatment image and the post-treatment image. The image displayed in the first image display portion $W_{21}$ as well as the second image display portion $W_{22}$ is a superimposed image formed by superimposing a narrow band light image and a fluorescence image. At that time, the size of the first image display portion $W_{21}$ and the second image display portion $W_{22}$ can be set in an appropriate manner, or the transmittance of the images at the time of superimposition of a narrow band light image and a fluorescence image can be set in an appropriate manner.

When the input portion 43 receives input of the determination result, the controller 44 determines whether or not the additional application of the treatment light is to be performed (Step S209). Based on the input determination result, if it is determined that the additional application of the treatment light is not required (No at Step S209), then the operations are ended. On the other hand, if it is determined that the additional application of the treatment light is required (Yes at Step S209), then the system control proceeds to Step S210.

In the case of performing the additional application of the treatment light, for example, in the illumination optical system, control is performed to match the shape of the light application range to the shape of the boundary region, and the operator adjusts the spot diameter and applies the treatment light.

The controller 44 determines whether or not, in the region on which the additional application of the treatment light is to be performed, the amount of already-applied light is within the acceptable range (Step S210). The acceptable range represents a preset amount of light and is set to have at least the upper limit value. The upper limit value is set so as to hold down any damage to the tissue due to excessive application of the treatment light. Thus, for example, the controller 44 determines whether or not the amount of light already applied onto the operator-specified target region (i.e., the cumulative amount of light) is exceeding the upper limit value.

If the controller 44 determines that the amount of light is within the acceptable range (i.e., smaller than the upper limit value) (Yes at Step S210), then the system control returns to Step S203 and the operations are repeated. At that time, from among the narrow band light images obtained before newly implementing the drug reaction process (Step S203), the latest narrow band light image is treated as the first narrow band light image before the treatment; and the narrow band light image obtained after the drug reaction process is treated as the second narrow band light image.

Meanwhile, if the controller 44 determines that the amount of already-applied light is exceeding the acceptable range (the upper limit value) (No at Step S210), then the system control proceeds to Step S211.

At Step S211, the controller 44 issues an alert indicating that the amount of applied light has exceeded the acceptable range. The alert can be displayed as character information in the display 5, or can be issued in the form of a sound or a light, or can be a combination thereof. After the alert is displayed in the display 5, the controller 44 ends the operations.

In the second embodiment described above, in an identical manner to the first embodiment, in the display 5, a superimposed image is displayed that is formed by superimposing a narrow band light image, in which the tissue structure is visualized, and a fluorescence image, in which the presence or absence of the antibody drug is visualized. Then, the operator is asked to determine whether or not the additional application of the treatment light is to be performed. According to the second embodiment, the effect of treatment can be appropriately confirmed not only based on the variation occurring in the tissue or the blood vessels after the treatment but also based on the residual state of the antibody drug.

Moreover, in the second embodiment, the variation between a pre-treatment image and a post-treatment image is calculated using narrow band light images or fluorescence images, and that variation is displayed. Then, the operator is asked to determine whether or not the additional application of the treatment light is to be performed. According to the second embodiment, regarding the variation in the tissue or the blood vessels before and after the treatment, the effect of treatment is calculated at the tissue level based on the narrow band light images in which the tissue and the blood vessels are visualized; and the variation occurring in the fluorescence, which is difficult to understand in a visual manner, is calculated as the amount of variation. As a result, it becomes possible to appropriately determine whether or not the additional application of the treatment light is to be performed onto the treatment region.

Third Embodiment

Figure 15:
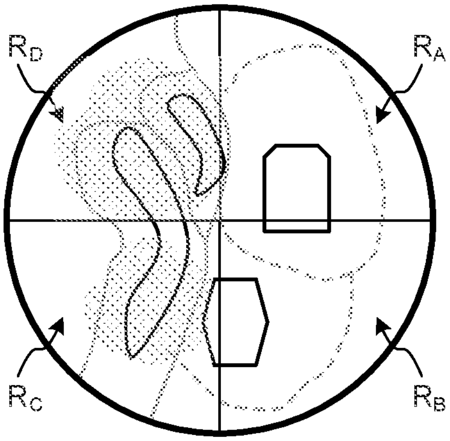
FIG. 15 is a diagram for explaining about a determination operation for determining the effect of treatment according to a third embodiment of the disclosure.

A third embodiment is described below with reference to FIG. 15. An endoscope system according to the third embodiment is identical to the endoscope system 1A according to the second embodiment. Hence, the same explanation is not given again. The following explanation is given about the operations that are different than the operations according to the second embodiment.

In the third embodiment, the image variation calculator 415 divides an image into a plurality of regions, and calculates the image variation occurring in each region. FIG. 15 is a diagram for explaining about a determination operation for determining the effect of treatment according to the third embodiment of the disclosure. In the example illustrated in FIG. 15, the image variation calculator 415 divides the pre-treatment image as well as the post-treatment image into four regions ($R_A$ to $R_D$), and calculates the image variation occurring in each region. In FIG. 15, the tissue in the regions $R_A$ and $R_B$ are in the normal state as a result of the treatment, but the tissue in the regions $R_C$ and $R_D$ still includes cancer cells and the antibody drug even after the treatment. The operator observes the narrow band light images and the image variation, and determines whether or not the additional application of the treatment light is to be performed in any region.

In the third embodiment described above, in an identical manner to the first embodiment, in the display 5, a superimposed image is displayed that is formed by superimposing a narrow band light image, in which the tissue structure is visualized, and a fluorescence image, in which the presence or absence of the antibody drug is visualized. Then, the operator is asked to determine whether or not the additional application of the treatment light is to be performed. According to the third embodiment, the effect of treatment can be appropriately confirmed not only based on the variation occurring in the tissue or the blood vessels after the treatment but also based on the residual state of the antibody drug.

Moreover, according to the third embodiment, the images are divided into a plurality of regions, and the image variation occurring in each region is calculated. Hence, it becomes possible to hold down excessive application of the treatment light onto the regions in which the treatment is complete. At the same time, the treatment light can be continually applied onto the regions in which the treatment is not yet complete.

Fourth Embodiment

Figure 16:
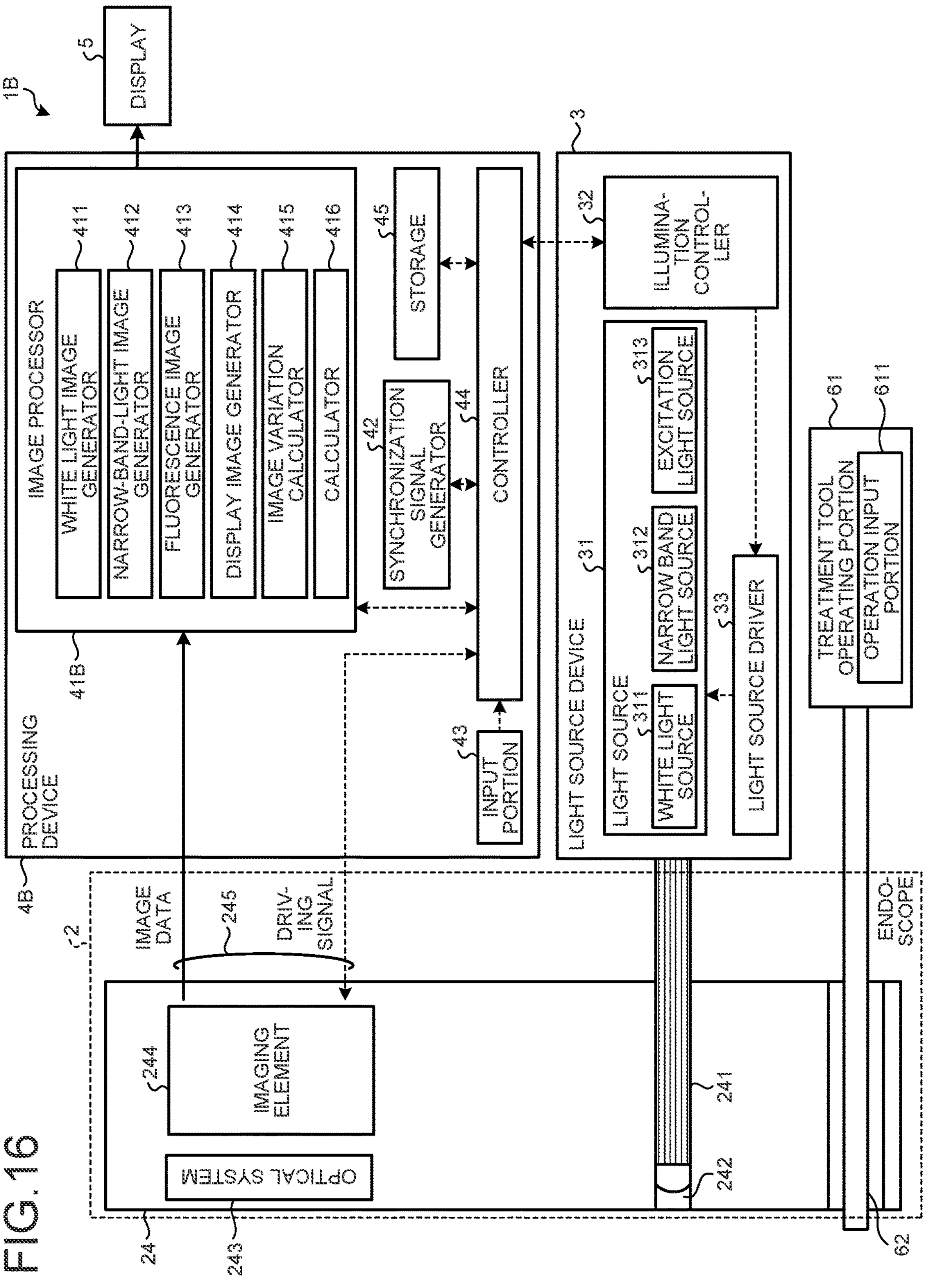
FIG. 16 is a block diagram illustrating an overall configuration of an endoscope system according to a fourth embodiment of the disclosure.

A fourth embodiment is described below with reference to FIG. 16. FIG. 16 is a block diagram illustrating an overall configuration of an endoscope system according to the fourth embodiment of the disclosure. An endoscope system 1B according to the fourth embodiment includes a processing device 4B in place of the processing device 4A of the endoscope system 1A according to the second embodiment. Other than the processing device 4B, the configuration is same as the endoscope system 1. Hence, the same explanation is not given again.

Given below is the explanation of a configuration of the processing device 4B. The processing device 4B includes an image processor 41B, the synchronization signal generator 42, the input portion 43, the controller 44, and the storage 45.

The image processor 41B includes the white light image generator 411, the narrow-band-light image generator 412, the fluorescence image generator 413, the display image generator 414, the image variation calculator 415, and a calculator 416.

The calculator 416 estimates the effect of treatment based on the image variation calculated by the image variation calculator 415. For example, the calculator 416 calculates the difference in the contrast values that is calculated as the image variation between the pre-treatment narrow band light image and the post-treatment narrow band light image; compares the difference with a preset threshold value; and estimates the effect of treatment. If the difference is smaller than the threshold value, then the calculator 416 estimates that the additional application of the treatment light is required. On the other hand, if the difference is equal to or greater than the threshold value, then the calculator 416 estimates that the treatment is complete. The estimation operation can be performed as the operation at Step S209 illustrated in FIG. 12. Alternatively, the estimation operation can be performed as part of the variation calculation operation at Step S206, and the estimation result can be displayed during the display process at Step S208.

In the case of displaying the estimation result during the display process at Step S208, the display image generator 414 generates an image by replacing the information displayed in the information display portion $W_{23}$ in the display image $W_2$ illustrated in FIG. 14 with the estimation result. Alternatively, the estimation result as well as the information about the image variation can be displayed in the image.

In the fourth embodiment described above, in an identical manner to the first embodiment, in the display 5, a superimposed image is displayed that is formed by superimposing a narrow band light image, in which the tissue structure is visualized, and a fluorescence image, in which the presence or absence of the antibody drug is visualized. Then, the operator is asked to determine whether or not the additional application of the treatment light is to be performed. According to the fourth embodiment, the effect of treatment can be appropriately confirmed not only based on the variation occurring in the tissue or the blood vessels after the treatment but also based on the residual state of the antibody drug.

Moreover, according to the fourth embodiment, the effect of treatment is estimated from the variation between the narrow band light images; and that estimation result can serve as the preferred determination criterion at the time of determining the effect of treatment by observing the narrow band light images and the image variation.

Fifth Embodiment

Figure 17A:
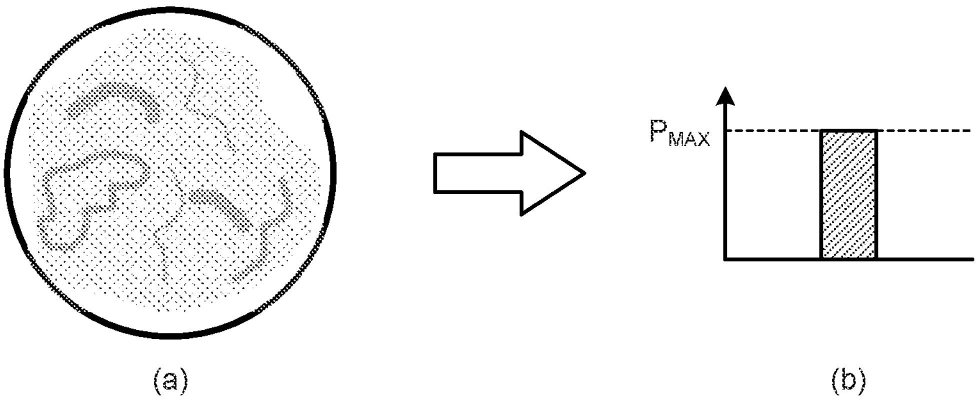
FIG. 17A is a diagram (1) for explaining an estimation operation performed according to a fifth embodiment of the disclosure.
Figure 17B:
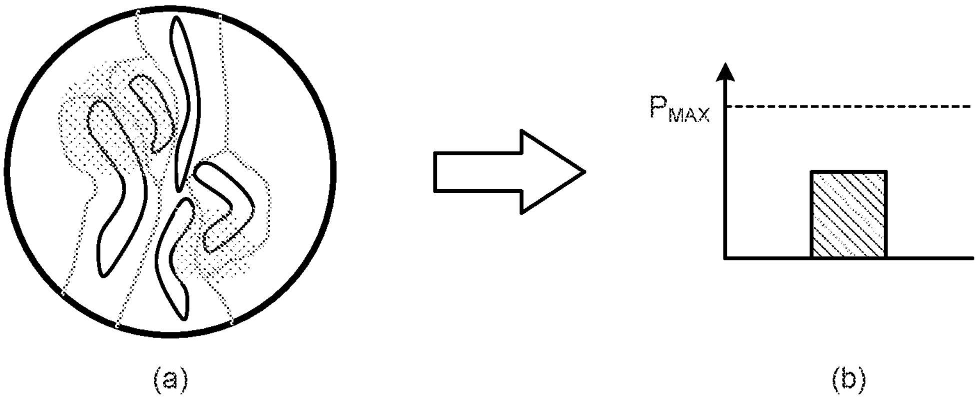
FIG. 17B is a diagram (2) for explaining the estimation operation performed according to the fifth embodiment of the disclosure.

A fifth embodiment is described below with reference to FIGS. 17A and 17B. An endoscope system according to the fifth embodiment is identical to the endoscope system 1B according to the fourth embodiment. Hence, the same explanation is not given again. The following explanation is given about the operations that are different than the operations according to the fourth embodiment.

In the fifth embodiment, the image variation calculator 415 either calculates the variation between the pre-treatment narrow band light image and the post-treatment narrow band light image, or calculates the image variation between the pre-treatment narrow band light image and a narrow band light image of the normal tissue as obtained in advance.

Based on the image variation calculated by the image variation calculator 415, the calculator 416 estimates the output (application intensity) of the treatment light. FIGS. 17A and 17B are diagrams for explaining an estimation operation performed according to the fifth embodiment of the disclosure. The calculator 416 estimates the intensity of the treatment light based on the magnitude of the image variation. For example, in the narrow band light image illustrated in (a) in FIG. 17A, when there is a large image variation with respect to the normal tissue, the calculator 416 sets the output of the treatment light to a maximum value $P_{MAX}$ (see (b) in FIG. 17A). In the narrow band light image illustrated in (a) in FIG. 17B, when there is only a small image variation with respect to the normal tissue, the calculator 416 sets the output of the treatment light to a smaller value than the maximum value $P_{MAX}$ (see (b) in FIG. 17B). At that time, a threshold value corresponding to the output value is set in advance with respect to the image variation. This estimation operation is either performed before the drug reaction process at Step S203 illustrated in FIG. 12, or performed after it is determined at Step S209 that additional application of the treatment light is required (Yes at Step S209).

In the case of displaying the estimation result, the display image generator 414 generates an image by displaying information indicating the output of the treatment light as the estimation result in the information display portion $W_{23}$ in the display images $W_2$ illustrated in FIG. 14. Alternatively, the estimation result as well as the information about the image variation can be displayed in the images.

The operator observes the narrow band light image and the image variation as well as refers to the estimated output value of the treatment light, and determines whether or not the additional application of the treatment light is to be performed in any region and determines the output (energy) of the treatment light.

In the fifth embodiment described above, in an identical manner to the first embodiment, in the display 5, a superimposed image is displayed that is formed by superimposing a narrow band light image, in which the tissue structure is visualized, and a fluorescence image, in which the presence or absence of the antibody drug is visualized. Then, the operator is asked to determine whether or not the additional application of the treatment light is to be performed. According to the fifth embodiment, the effect of treatment can be appropriately confirmed not only based on the variation occurring in the tissue or the blood vessels after the treatment but also based on the residual state of the antibody drug.

Moreover, according to the fifth embodiment, the output of the treatment light is estimated based on the narrow band light images, and the estimation result can serve as the preferred determination criterion at the time of applying the treatment light.

Sixth Embodiment

A sixth embodiment is explained below with reference to FIGS. 18A and 18B. An endoscope system according to the sixth embodiment is identical to the endoscope system 1B according to the fourth embodiment. Hence, the same explanation is not given again. The following explanation is given about the operations that are different than the operations according to the fourth embodiment.

In the sixth embodiment, the image variation calculator 415 either calculates the variation between the pre-treatment narrow band light image and the post-treatment narrow band light image, or calculates the image variation between the pre-treatment narrow band light image and a narrow band light image of the normal tissue as obtained in advance.

Based on the image variation calculated by the image variation calculator 415, the calculator 416 estimates the required application intensity of the treatment light. FIGS. 18A and 18B are diagrams for explaining an estimation operation performed according to the sixth embodiment of the disclosure. The calculator 416 estimates the application period of the treatment light based on the magnitude of the image variation. At that time, the treatment light is assumed to be at a preset output. For example, in the narrow band light image illustrated in (a) in FIG. 18A, when there is a large image variation with respect to the normal tissue, the calculator 416 sets the application period to, for example, 70 minutes according to the magnitude of the image variation. In the narrow band light image illustrated in (a) in FIG. 18B, when there is a relatively small image variation with respect to the normal tissue, the calculator 416 sets the application period to, for example, 15 minutes. At that time, a threshold value corresponding to the application period is set in advance with respect to the image variation. This estimation operation is either performed before the drug reaction process at Step S203 illustrated in FIG. 12, or performed after it is determined at Step S209 that the additional application of the treatment light is required (Yes at Step S209).

Figure 18A:
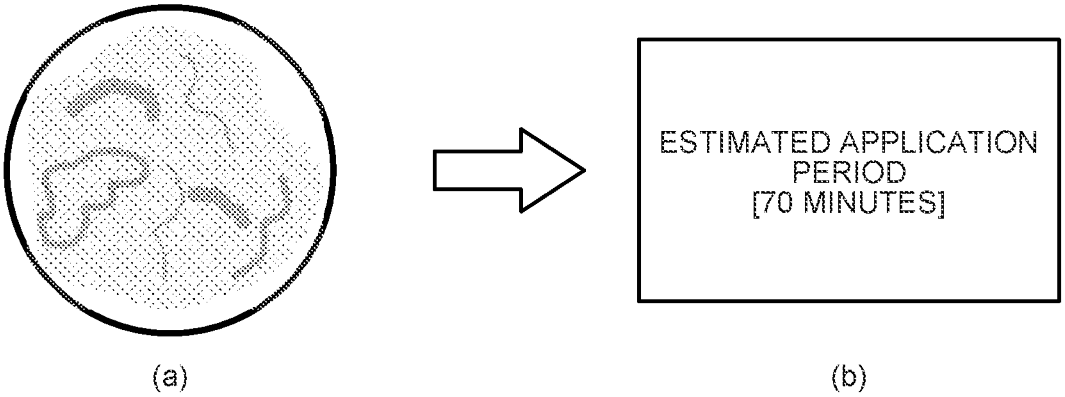
FIG. 18A is a diagram (1) for explaining an estimation operation performed according to a sixth embodiment of the disclosure.
Figure 18B:
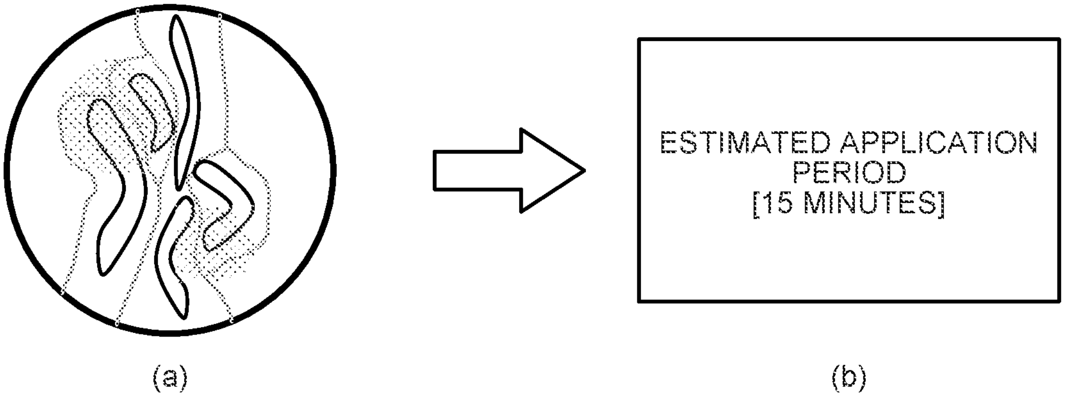
FIG. 18B is a diagram (2) for explaining the estimation operation performed according to the sixth embodiment of the disclosure.

In the case of displaying the estimation result, the display image generator 414 generates an image by displaying information indicating the application period of the treatment light as the estimation result in the information display portion $W_{23}$ in the display image $W_2$ illustrated in FIG. 14 (for example, see (b) in FIGS. 18A and (b) in FIG. 18B). Alternatively, the estimation result as well as the information about the image variation can be displayed in the images.

The operator observes the narrow band light images and the image variation as well as refers to the estimated application period of the treatment light, and determines whether or not the additional application of the treatment light is to be performed in any region and determines the application period of the treatment light.

In the sixth embodiment described above, in an identical manner to the fourth embodiment, the variation between the pre-treatment tissue and the post-treatment tissue is calculated using the narrow band light images, and information is displayed based on that variation. Then, the operator is asked to determine whether or not the additional application of the treatment light is to be performed. According to the sixth embodiment, regarding the variation in the tissue or the blood vessels before and after the treatment, the effect of treatment is calculated at the tissue level based on the narrow band light images in which the tissue and the blood vessels are visualized. That enables appropriate application of light onto the treatment region.

Moreover, according to the sixth embodiment, the treatment light application period is estimated based on the narrow band light images, and the estimation result can serve as the preferred determination criterion at the time of applying the treatment light.

Meanwhile, the sixth embodiment can be combined with the fifth embodiment, and the output of the treatment light and the application period of the treatment light can be combinedly output as the estimation result.

Moreover, in the fifth and sixth embodiments described above, a narrow band light image meant for comparison can be prepared in advance in a corresponding manner to the output of the treatment light or the application period of the treatment light, and the calculator 416 can compare the features of the narrow band light image meant for comparison with the feature quantity of the narrow band light image to be processed, and accordingly estimate the output of the treatment light or the application period of the treatment light.

Seventh Embodiment

Figure 19:
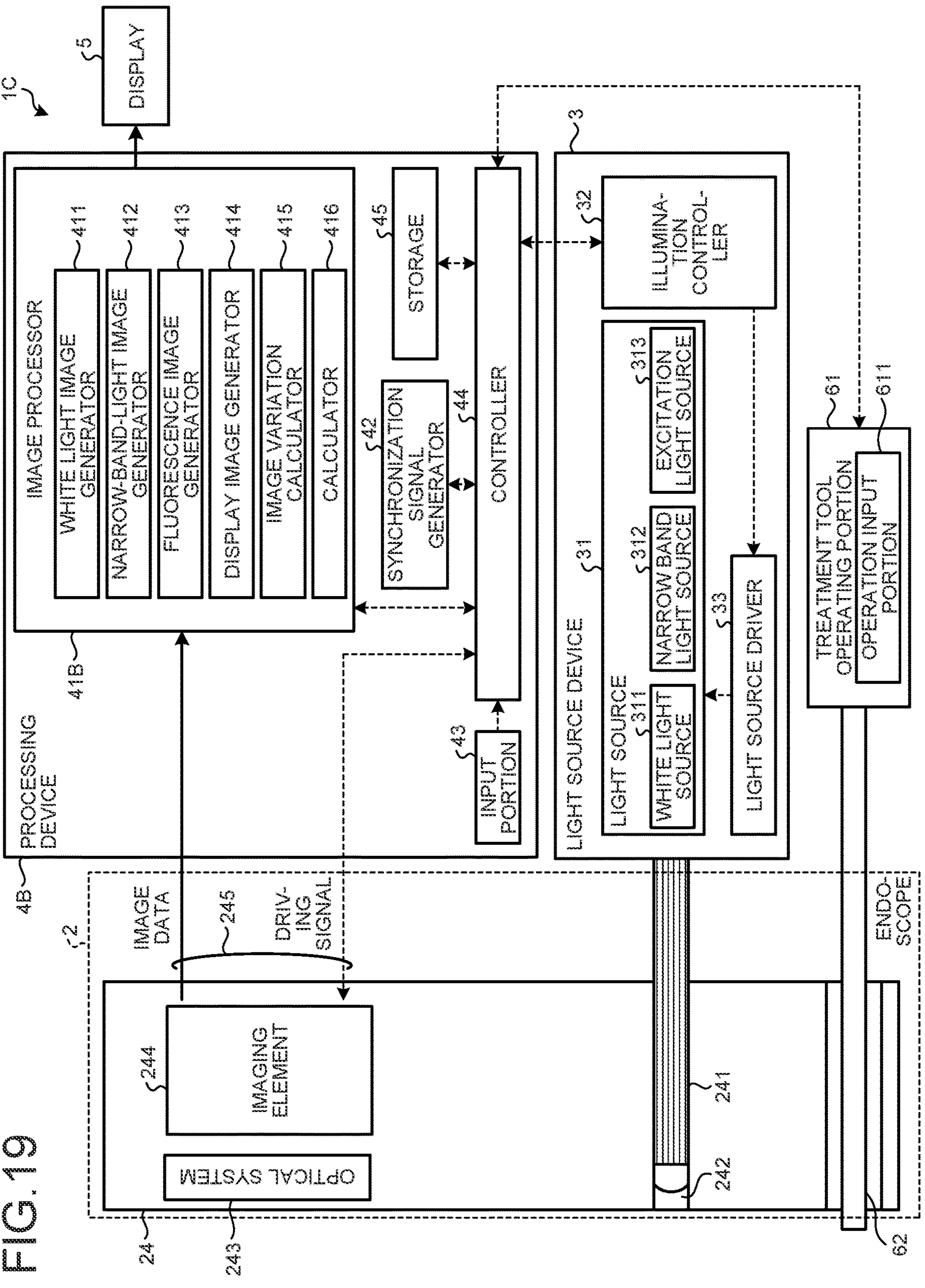
FIG. 19 is a block diagram illustrating an overall configuration of an endoscope system according to a seventh embodiment of the disclosure.

A seventh embodiment is described below with reference to FIG. 19. FIG. 19 is a block diagram illustrating an overall configuration of an endoscope system according to the seventh embodiment of the disclosure. An endoscope system 1C according to the seventh embodiment has an identical configuration to the endoscope system 1B according to the fourth embodiment. In the endoscope system 1C, the processing device 4B is electrically connected to the treatment tool device 6, and the controller 44 of the processing device 4 controls the emission of the treatment light from the treatment tool 62.

In the case of implementing photoimmunotherapy, the processing device 4B performs operations according to the flow illustrated in FIG. 12. At the time of applying the treatment light, the controller 44 controls the application range, the application timing, and the application period of the treatment light. More particularly, for example, with respect to the application range set by the operator, the controller 44 sets a light intensity (output value) representing a preset amount of applied light, and sets the application period. In response to the pressing of a switch of the operation input portion 611, the controller 44 starts the application control of the treatment light. At the time of additional application of the treatment light, the controller 44 sets the shape of the application range of the treatment light, which is emitted from the treatment tool 62, according to the target boundary region; and, in response to the pressing of a switch of the operation input portion 611, starts the application control of the treatment light.

Meanwhile, in the seventh embodiment, the controller 44 performs control according to the flowchart illustrated in FIG. 12 so as to ensure that the narrow band light and the treatment light are alternately emitted. Alternatively, the narrow band light and the treatment light can be emitted in a simultaneous manner.

In the seventh embodiment described above, in an identical manner to the fourth embodiment, the variation between the pre-treatment tissue and the post-treatment tissue is calculated using the narrow band light images, and information is displayed based on that variation. Then, the operator is asked to determine whether or not the additional application of the treatment light is to be performed. According to the seventh embodiment, regarding the variation in the tissue or the blood vessels before and after the treatment, the effect of treatment is calculated at the tissue level based on the narrow band light images in which the tissue and the blood vessels are visualized. As a result, it becomes possible to appropriately determine whether or not the treatment light needs to be applied again onto the treatment region.

Moreover, according to the seventh embodiment, since the application of the treatment light is controlled by the controller 44, it becomes possible to reduce the burden on the operator.

In the first to seventh embodiments described above, the explanation is given about the example in which the light source device 3 and the processing device 4 are separate devices. Alternatively, the light source device 3 and the processing device 4 can be integrated into a single device. Moreover, in the first to seventh embodiments described above, the explanation is given about the example in which the treatment light is applied using a treatment tool. Alternatively, the light source device 3 can be configured to emit the treatment light.

Moreover, in the first to seventh embodiments described above, the excitation light and the treatment light either can have the same frequency band (the same central frequency), or can have mutually different frequency bands (central frequencies). Meanwhile, when the excitation light is used in common with the treatment light, it serves the purpose as long as the treatment light (the excitation light) is applied using the treatment tool 62 or the excitation light source. Hence, either the excitation light source or the treatment tool 62 can be omitted from the configuration. In the case of causing excitation of an antibody drug in photoimmunotherapy, for example, the near-infrared light $L_P$ having the central wavelength of 690 nm is used.

Furthermore, in the first to seventh embodiments described above, the endoscope system 1, which treats the body tissue inside a subject as the observation target and which includes the flexible endoscope 2, represents the endoscope system according to the disclosure. Alternatively, it is also possible to use an endoscope system in which a rigid endoscope is used, or an industrial endoscope is used for observing the characteristic features of materials, or a fiberscope is used, or such a device is used in which a camera head is connected to the eyepiece of an optical endoscope such as an optical viewing tube.

Note

A phototherapy method including:

administering a drug, which is to be used in phototherapy, to a treatment area;

applying treatment light onto the treatment area to cause the drug, which is bound to the treatment area, to react;

applying narrow band light onto the treatment area to obtain a post-treatment narrow band light image;

applying excitation light onto the treatment area to obtain a post-treatment fluorescence image;

generating a superimposed image in which the narrow band light image and the fluorescence image are superimposed; and referring to the superimposing image to determine whether or not to continue an application of the treatment light.

As explained above, a phototherapy device, a phototherapy method, and a computer-readable recording medium according to the disclosure are useful in confirming the effect of treatment in an appropriate manner.

According to the disclosure, it becomes possible to confirm the effect of treatment in an appropriate manner.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A phototherapy device comprising:

a treatment light emitter configured to emit treatment light for causing a reaction of a drug;

a narrow band light emitter configured to emit narrow band wavelength light having part of a wavelength band of a visible light range;

an excitation light emitter configured to emit excitation light for causing excitation of the drug;

a first imager configured to obtain a narrow band light image which is formed using the narrow band wavelength light applied onto an application position of the treatment light;

a second imager configured to obtain a fluorescence image which is formed using the excitation light emitted onto the application position of the treatment light;

an image variation calculator configured to calculate a time variation between the narrow band light image before an application of the treatment light and the narrow band light image after the application of the treatment light; and a display image generator configured to generate a superimposed image in which the narrow band light image and the fluorescence image are superimposed.

2. The phototherapy device according to claim 1, wherein the image variation calculator is configured to calculate a time variation between a fluorescence intensity of the fluorescence image before the application of the treatment light and a fluorescence intensity of the fluorescence image after the application of the treatment light.

3. The phototherapy device according to claim 1, wherein the display image generator is configured to generate the superimposed image by superimposing the narrow band light image and the fluorescence image with brightness or transmittance set in each of the narrow band light image and the fluorescence image.

4. The phototherapy device according to claim 1, wherein the image variation calculator is configured to divide the narrow band light image into a plurality of regions, and calculate an amount of variation occurring in an image in each region obtained by division.

5. The phototherapy device according to claim 1, wherein the display image generator is configured to generate a display image in which the superimposed image obtained before an application of the treatment light is lined up with the superimposed image obtained after the application of the treatment light.

6. The phototherapy device according to claim 1, further comprising a treatment light calculator configured to estimate an output of the treatment light based on the variation calculated by the image variation calculator.

7. The phototherapy device according to claim 1, further comprising a treatment light calculator configured to estimate an application period of the treatment light based on the variation calculated by the image variation calculator.

8. A phototherapy method implemented for applying treatment light, which causes a reaction of a drug, onto a treatment area to confirm an effect of treatment, the phototherapy method comprising:

obtaining a narrow band light image formed using narrow band wavelength light that is emitted onto an application position of treatment light causing a reaction of a drug, the narrow band wavelength light having part of wavelength band of a visible light range;

obtaining a fluorescence image formed using excitation light that is emitted onto the application position of the treatment light and that causes excitation of the drug;

calculating a time variation between the narrow band light image before an application of the treatment light and the narrow band light image after the application of the treatment light; and generating a superimposed image in which the narrow band light image and the fluorescence image are superimposed and an image in which the calculated time variation is visually expressed.

9. A non-transitory computer-readable recording medium that stores a computer program to be executed by a phototherapy device applying treatment light, which causes a reaction of a drug, onto a treatment area to generate information to be used in confirming an effect of treatment, the program causing the phototherapy device to execute:

obtaining a narrow band light image formed using narrow band wavelength light that is emitted onto an application position of treatment light causing a reaction of a drug, the narrow band wavelength light having part of wavelength band of a visible light range;

obtaining a fluorescence image formed using excitation light that is emitted onto the application position of the treatment light and that causes excitation of the drug;

calculating a time variation between the narrow band light image before an application of the treatment light and the narrow band light image after the application of the treatment light; and generating a superimposed image in which the narrow band light image and the fluorescence image are superimposed and an image in which the calculated time variation is visually expressed.

* * * * *